US012653760B2

(12) United States Patent
Spivak et al.

(10) Patent No.: US 12,653,760 B2
(45) Date of Patent: Jun. 16, 2026

(54) NIPPLE SHIELD WITH PORT AND FLAP-COVERED CHANNEL TO SUPPLEMENT LACTATION DURING BREASTFEEDING

(71) Applicant: Neotech Products LLC, Valencia, CA (US)

(72) Inventors: Yekaterina Spivak, Mountainside, NJ (US); Maksim Spivak, Mountainside, NJ (US); Aaron Bronshtein, Oakland, NJ (US); Michael Maloney, Caledon East (CA)

(73) Assignee: Neotech Products LLC, Valencia, CA (US)

( * ) Notice: Subject to any disclaimer, the term of this patent is extended or adjusted under 35 U.S.C. 154(b) by 0 days.

(21) Appl. No.: 18/826,922

(22) Filed: Sep. 6, 2024

(65) Prior Publication Data

US 2025/0009605 A1    Jan. 9, 2025

Related U.S. Application Data

(62) Division of application No. 16/830,098, filed on Mar. 25, 2020, now Pat. No. 12,083,074.

(51) Int. Cl.
*A61J 13/00* (2006.01)
*A61J 11/00* (2006.01)
*A61J 15/00* (2006.01)
*A61M 1/06* (2006.01)

(52) U.S. Cl.
CPC ........... *A61J 13/00* (2013.01); *A61J 11/0005* (2013.01); *A61J 15/0053* (2013.01); *A61M 1/068* (2014.02)

(58) Field of Classification Search
CPC ...... A61J 11/00; A61J 11/0005; A61J 11/001; A61J 11/0015; A61J 11/002; A61J 11/0035; A61J 11/0045; A61J 11/005; A61J 11/0055; A61J 11/02; A61J 13/00; A61J 15/0026; A61J 15/0053; A61J 15/0057; A61J 15/0061; A61J 15/0065; A61J 7/00; A61F 13/14; A61F 13/141; A61F 13/145;

(Continued)

(56) References Cited

U.S. PATENT DOCUMENTS 4,547,192 A    10/1985 Brodsky
4,687,466 A    8/1987 Larsson (Continued)

FOREIGN PATENT DOCUMENTS

IT    BO20110704 A1    6/2013

*Primary Examiner* — Alireza Nia
*Assistant Examiner* — Gina Mccarthy
(74) *Attorney, Agent, or Firm* — Michael A. DiNardo; YK LAW LLP

(57) ABSTRACT

Nipple shields can be used by breastfeeding mothers to facilitate the feeding process. The disclosed embodiments relate to nipple shields with a port through which liquid supplement can flow from a supply tube into an interior section of the shield. The liquid supplement can be drawn through ports in a tip of the shield in order to augment a naturally expressed flow of milk. A flap of material is bonded to an interior portion of the nipple shield over an optional channel formed in the interior portion so as to form a closed, flap-covered channel leading from an input port on a lower portion of the shield to an interior location near the tip of the shield.

10 Claims, 28 Drawing Sheets

(58) Field of Classification Search
CPC .. A61M 1/06; A61M 1/062; A61M 1/064068;
A61M 1/069
See application file for complete search history.

(56) References Cited

U.S. PATENT DOCUMENTS

| | | | |
|---|---|---|---|
| 5,080,650 A * | 1/1992 | Hirsch | .............. A61J 15/0038 |
| | | | 604/525 |
| D384,414 S | 9/1997 | Pernarella | |
| 6,270,519 B1 | 8/2001 | Botts | |
| D476,085 S | 6/2003 | Dumont et al. | |
| D483,491 S | 12/2003 | Grady et al. | |
| 6,968,964 B2 | 11/2005 | Gilmore | |
| D584,399 S | 1/2009 | Pacini | |
| D599,028 S | 8/2009 | Schofield | |
| 8,357,117 B2 | 1/2013 | Sokal et al. | |
| 8,469,771 B2 | 6/2013 | Francis | |
| 8,672,877 B2 | 3/2014 | Gust | |
| 9,060,917 B1 | 6/2015 | Tronson | |
| D780,610 S | 3/2017 | Ogden | |
| D798,460 S | 9/2017 | Farley | |
| D810,308 S | 2/2018 | Lind et al. | |
| 9,895,292 B1 | 2/2018 | Tronson | |
| 10,016,341 B2 | 7/2018 | Chin et al. | |
| 10,149,801 B2 | 12/2018 | Conner et al. | |
| D876,645 S | 2/2020 | Zhang | |
| 10,639,207 B1 | 5/2020 | Harder et al. | |
| D887,011 S | 6/2020 | Wei | |
| D913,506 S | 3/2021 | Ladiges | |
| D914,892 S | 3/2021 | Spivak et al. | |
| 2004/0182813 A1* | 9/2004 | Gilmore | .............. A61J 11/0005 |
| | | | 215/11.4 |
| 2006/0100603 A1 | 5/2006 | Thwaits | |
| 2006/0149292 A1 | 7/2006 | Knudtson | |
| 2006/0226108 A1 | 10/2006 | Dahan et al. | |
| 2009/0166481 A1 | 7/2009 | Chen | |
| 2013/0270140 A1 | 10/2013 | Tronson | |
| 2015/0005678 A1 | 1/2015 | Wall | |
| 2016/0120763 A1 | 5/2016 | Conner et al. | |
| 2016/0288983 A1* | 10/2016 | Chin | .................... A61J 7/0015 |
| 2019/0008727 A1* | 1/2019 | Seaward | ................. A61J 13/00 |
| 2021/0169398 A1* | 6/2021 | Sorgini | .................... G01F 1/69 |

\* cited by examiner

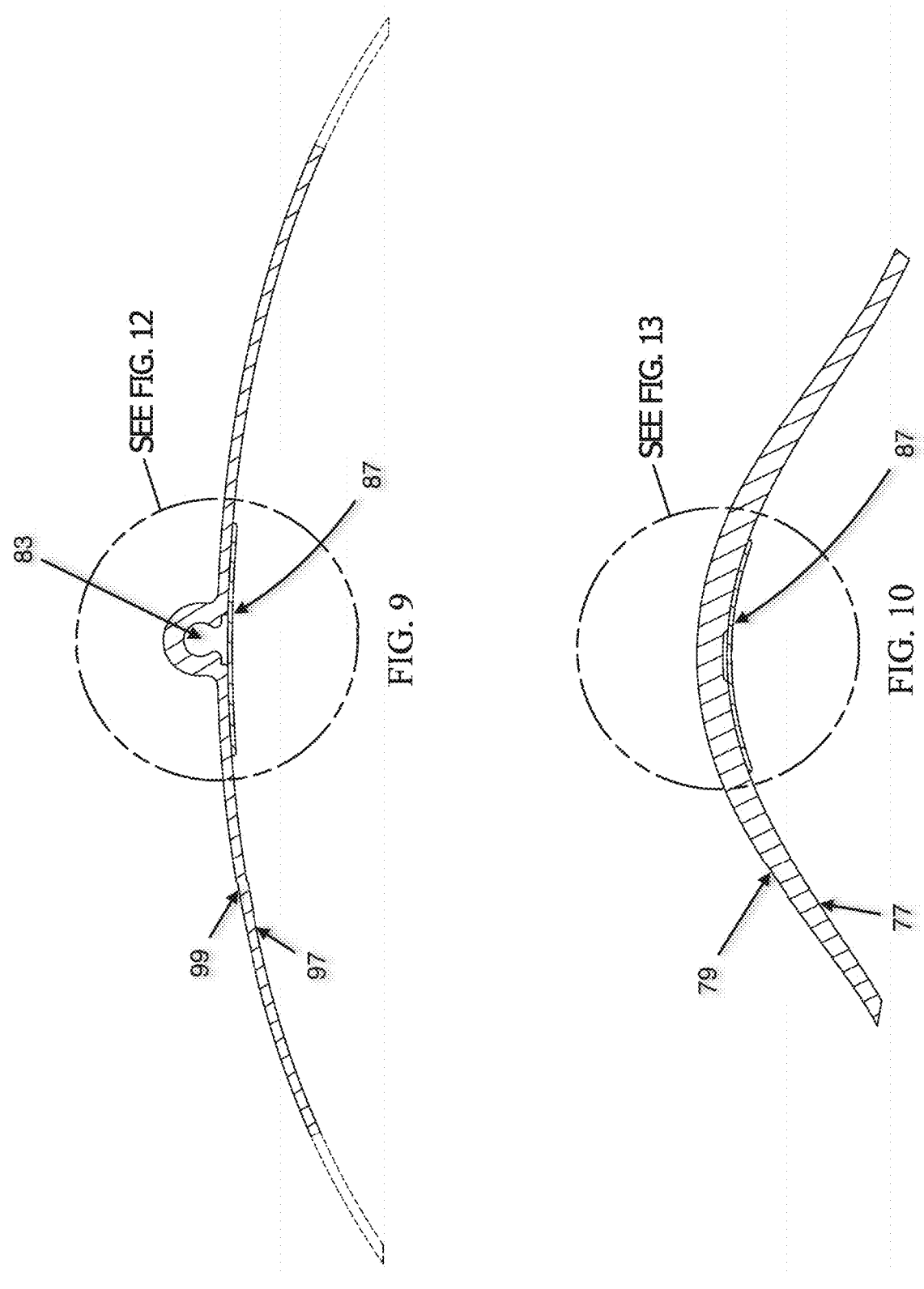

SEE FIG. 26

83

SEE FIG. 27

NIPPLE SHIELD WITH PORT AND FLAP-COVERED CHANNEL TO SUPPLEMENT LACTATION DURING BREASTFEEDING

RELATED APPLICATIONS

This is a divisional of co-pending U.S. application Ser. No. 16/830,098, filed on Mar. 25, 2020.

BACKGROUND OF THE INVENTION

Nipple shields can be used by breastfeeding mothers to facilitate the feeding process.

SUMMARY OF THE INVENTION

The disclosed embodiments relate to nipple shields with a port through which liquid supplement can flow from a supply tube into an interior section of the shield. The liquid supplement can be drawn through ports in a tip of the shield in order to augment a naturally expressed flow of milk. A flap of material is bonded to an interior portion of the nipple shield over an optional channel formed in the interior portion so as to form a closed, flap-covered channel leading from an input port on a lower portion of the shield to an interior location near the tip of the shield.

BRIEF DESCRIPTION OF THE DRAWINGS

FIGS. 1-14 illustrate an assembled nipple shield with a flap that is bonded in place according to a first embodiment.

Figure 1:
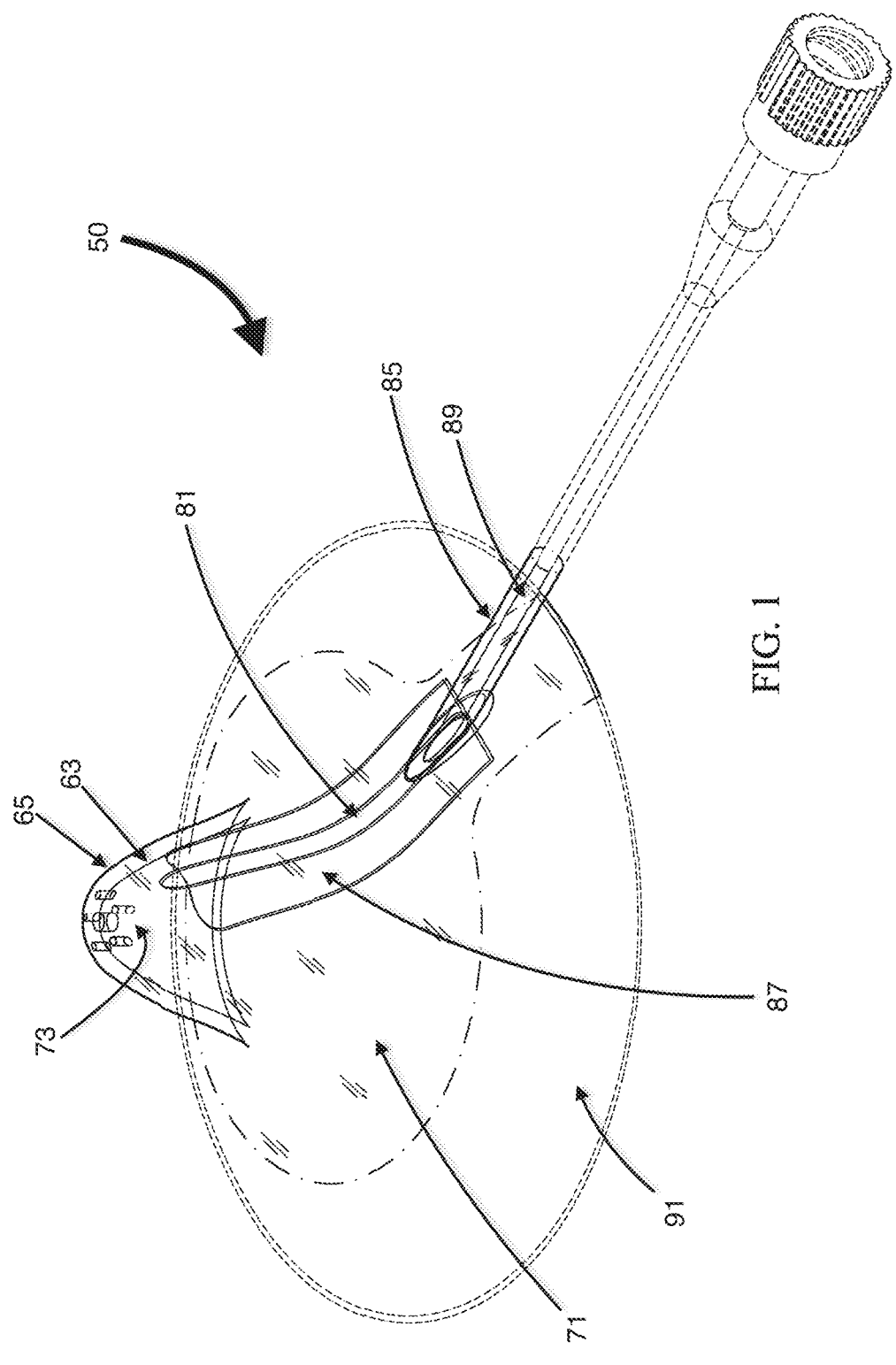

In the drawings, broken lines illustrate primarily environmental structure that is nevertheless within the scope of the present disclosure. The dot-dash broken lines in the drawings delineate different portions of the embodiments and can be ignored since they do not represent any particular structure or markings thereon. The short-short-long dash broken lines identify cross section views and enlarged views of the embodiments.

FIG. 1 is a perspective view.

Figure 2:
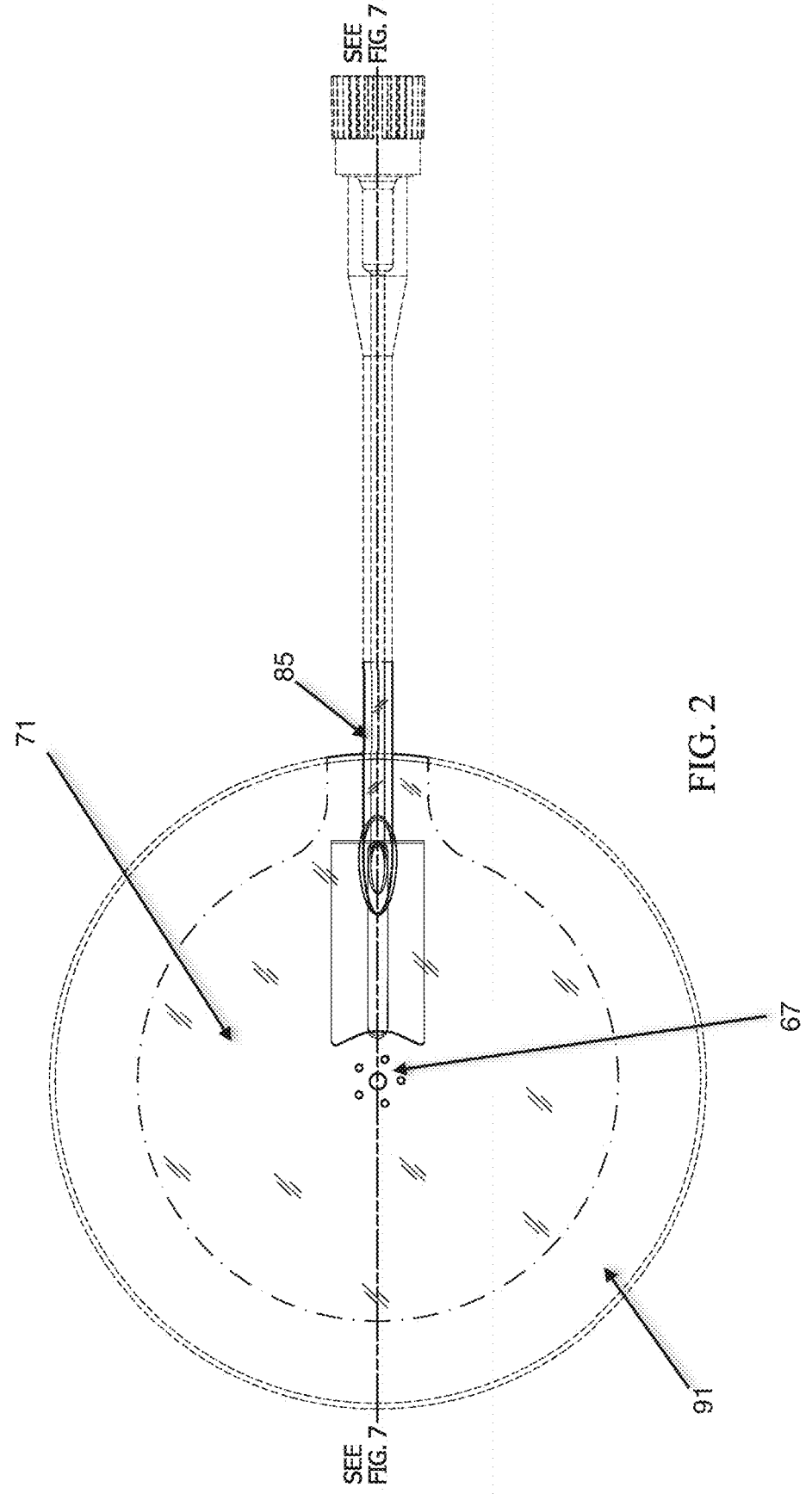

FIG. 2 is a top view (exterior).

Figure 3:
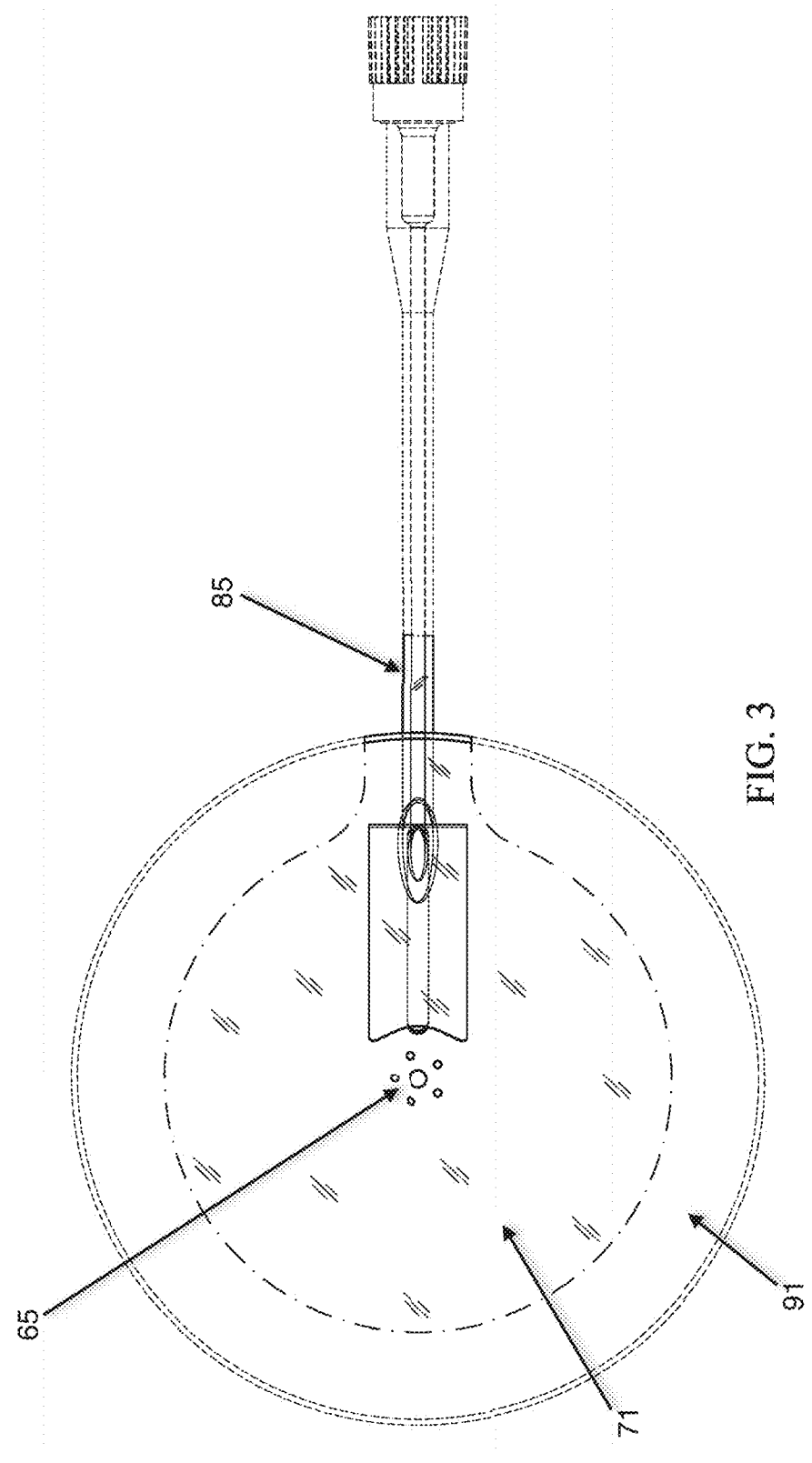

FIG. 3 is a bottom view (interior).

Figure 4:
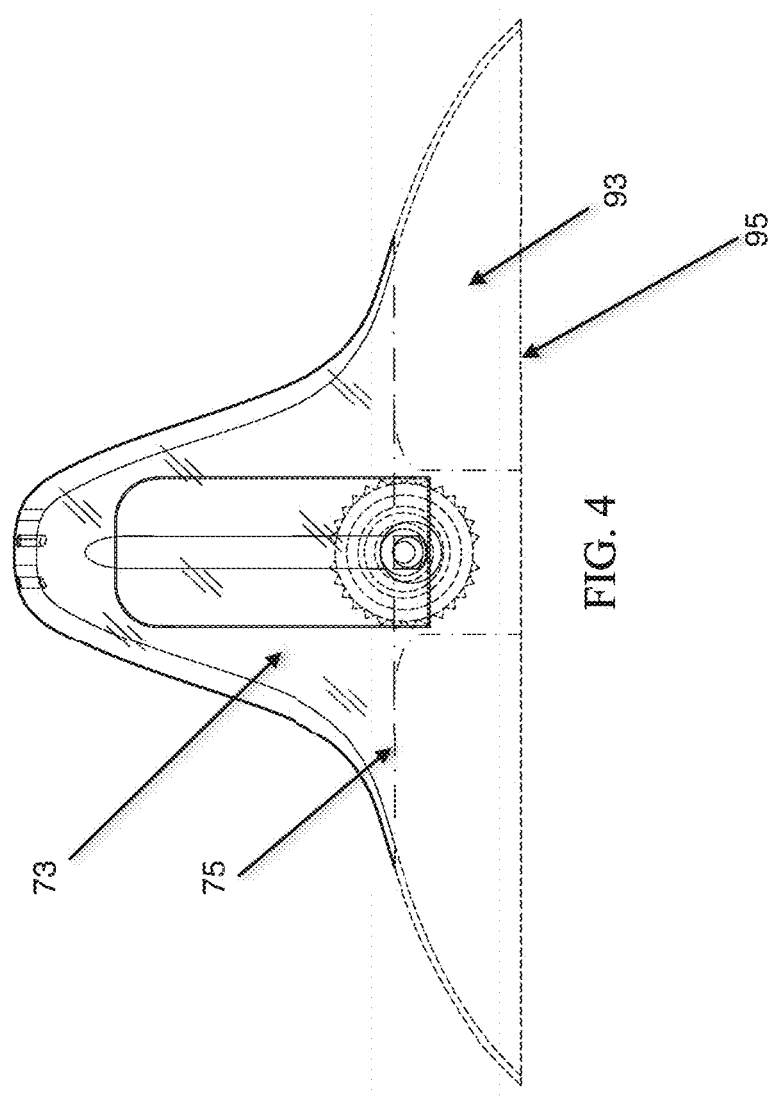

FIG. 4 is front view (opposite the port and tube).

Figure 5:
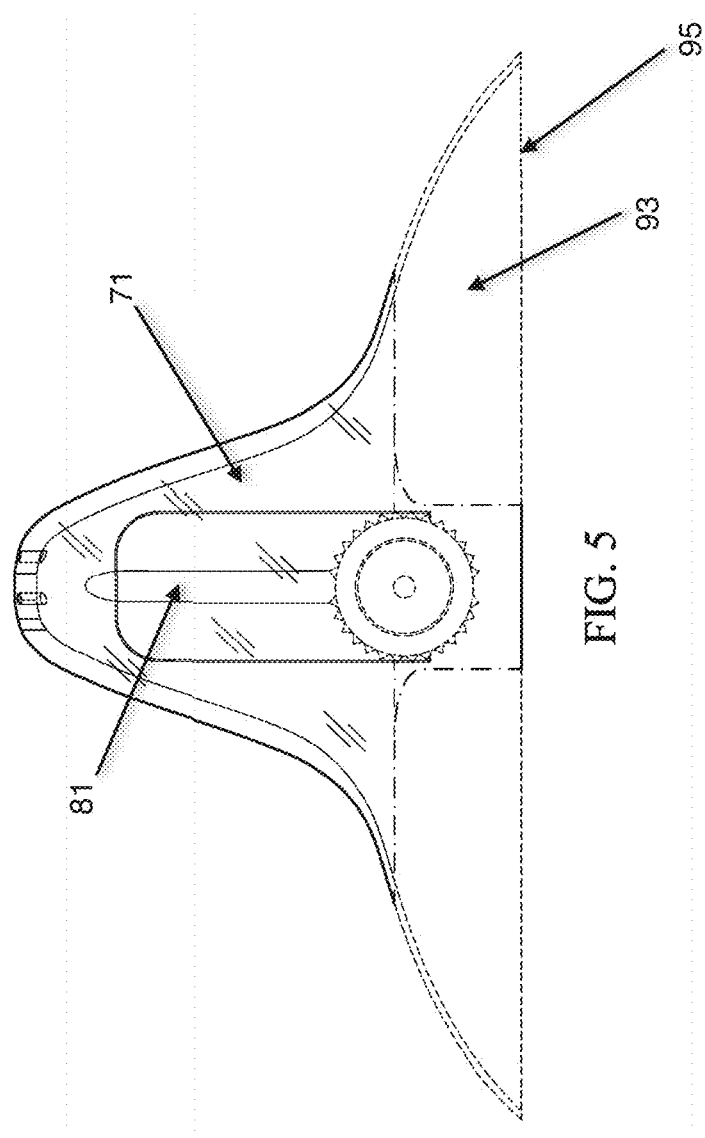

FIG. 5 is a back view (proximate the port and tube).

Figure 6:
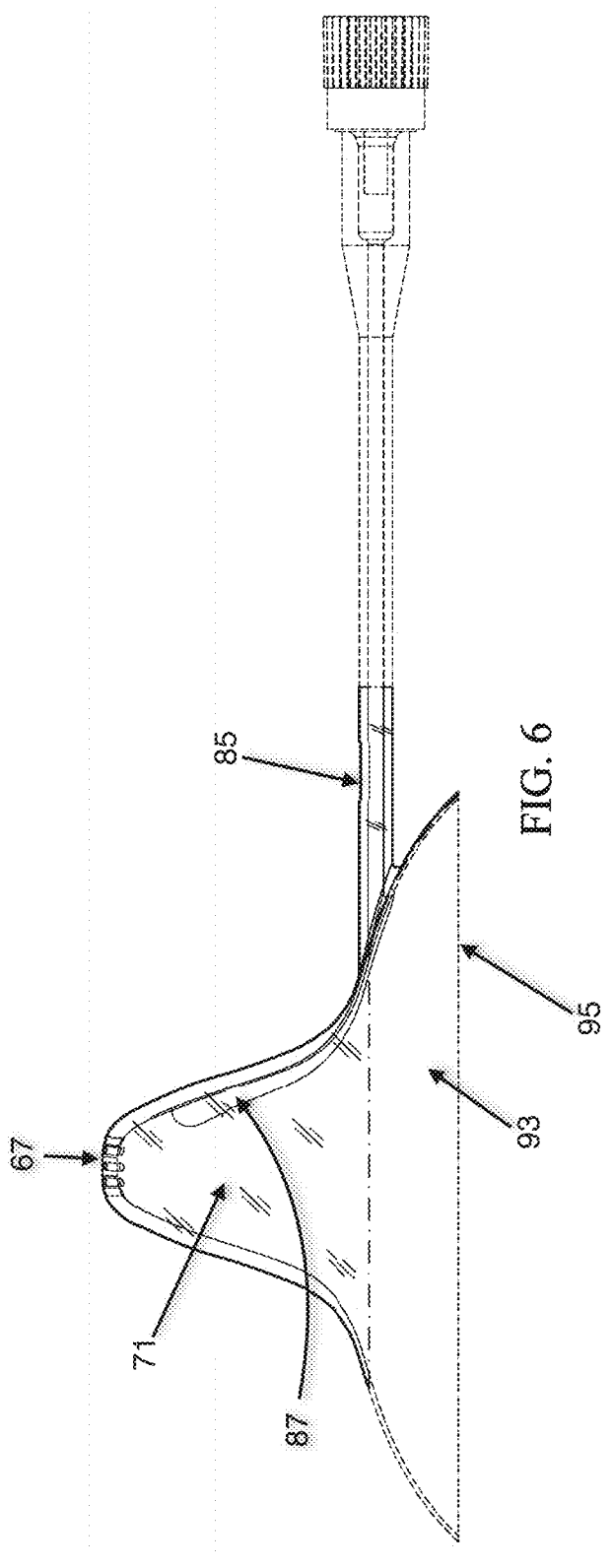

FIG. 6 is a right side view, and the left side view (not illustrated) is a mirror image of the right side view.

Figure 7:
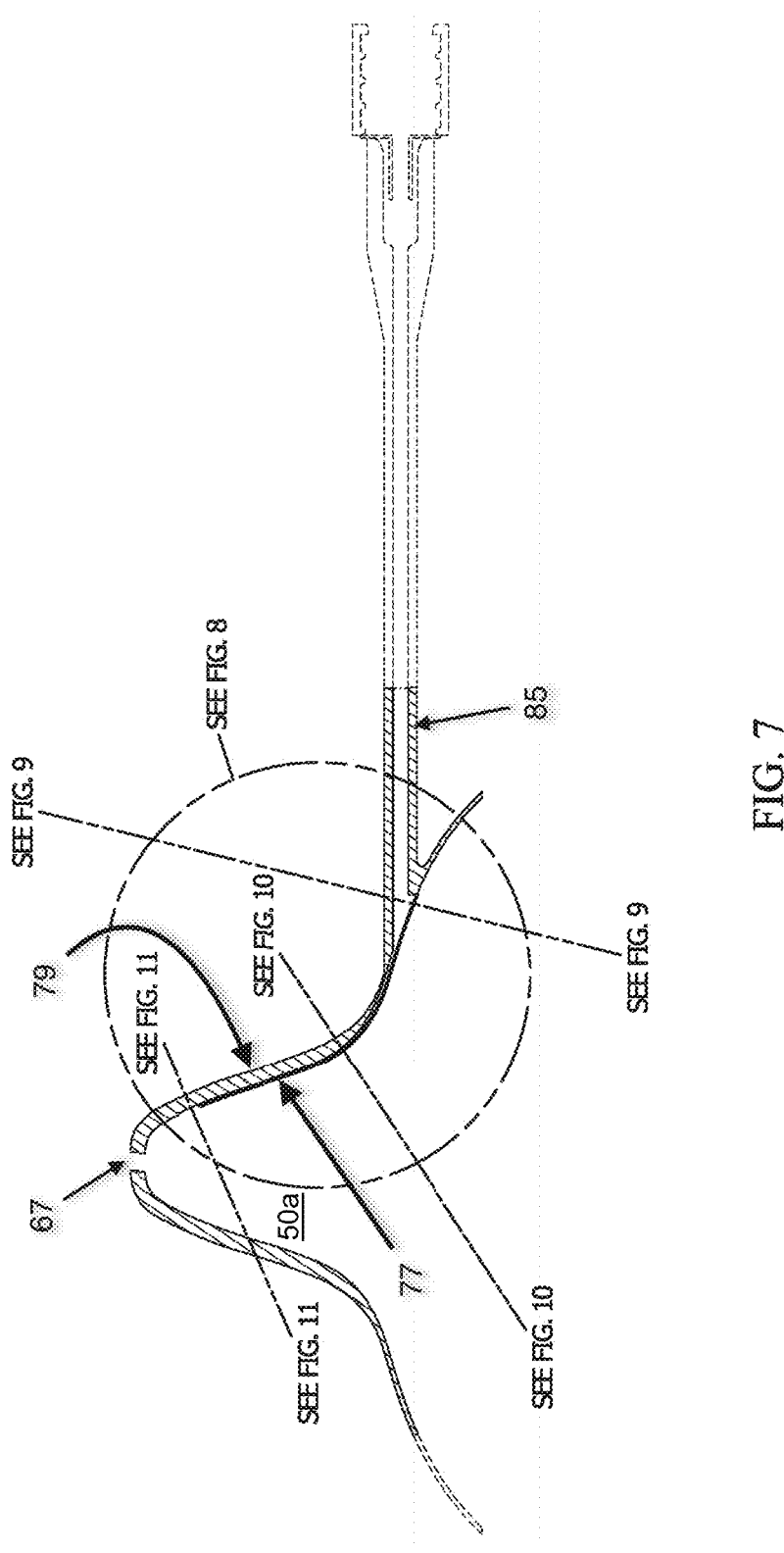

FIG. 7 is a cross-section view along the short-short-long dash line indicated in FIG. 2.

Figure 8:
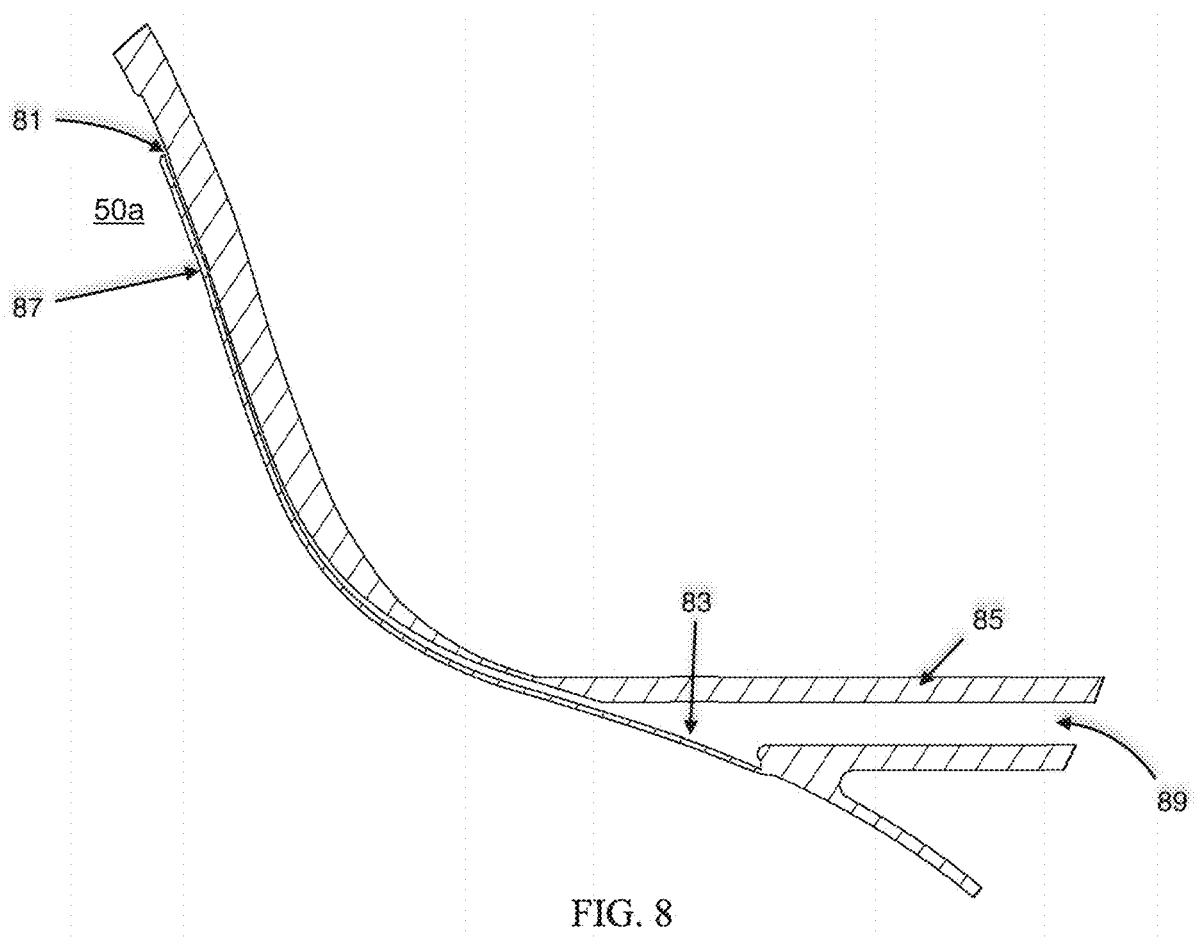

FIG. 8 is an enlarged view of the encircled area indicated in FIG. 7.

FIG. 9 is a cross-section view along the correspondingly numbered short-short-long dash line indicated in FIG. 7.

FIG. 10 is a cross-section view along the correspondingly numbered short-short-long dash line indicated in FIG. 7.

Figures 11, 12:
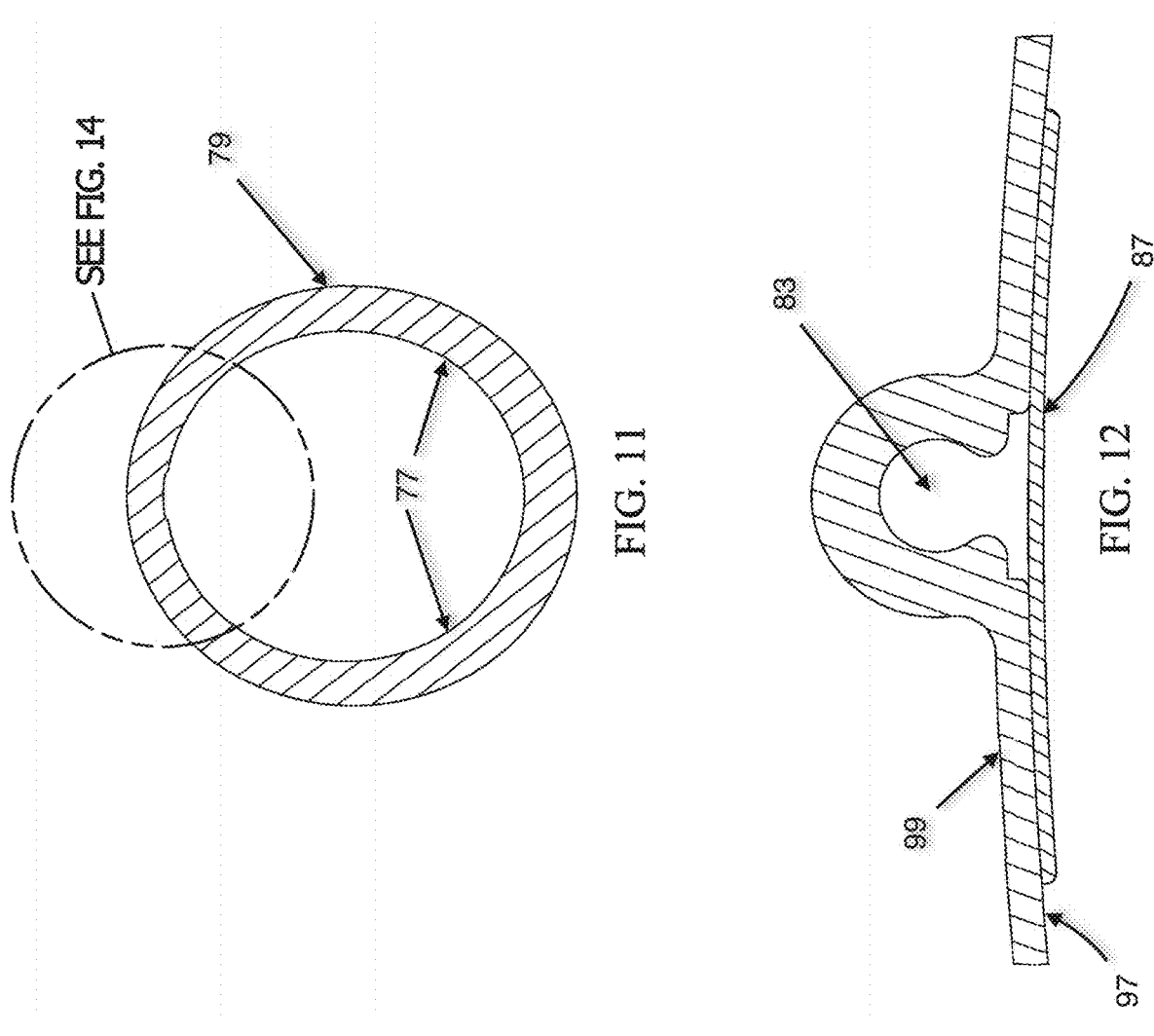

FIG. 11 is a cross-section view along the correspondingly numbered short-short-long dash line indicated in FIG. 7.

FIG. 12 is an enlarged view of the encircled area indicated in FIG. 9.

Figure 13:
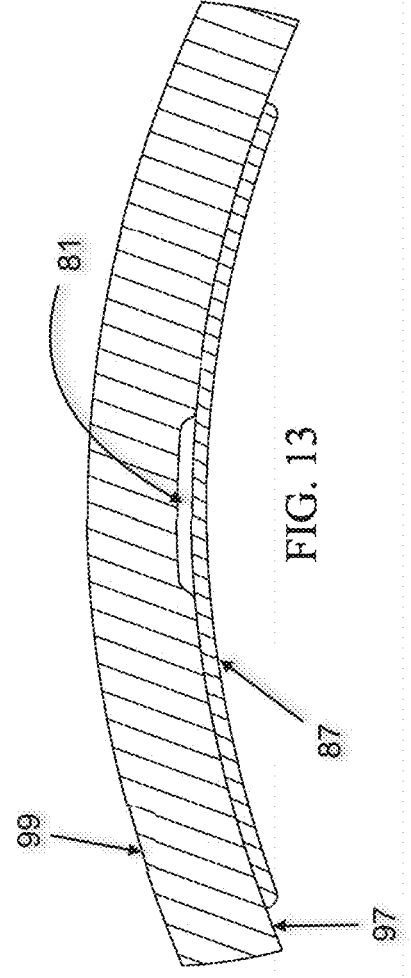

FIG. 13 is an enlarged view of the encircled area indicated in FIG. 10.

Figure 14:
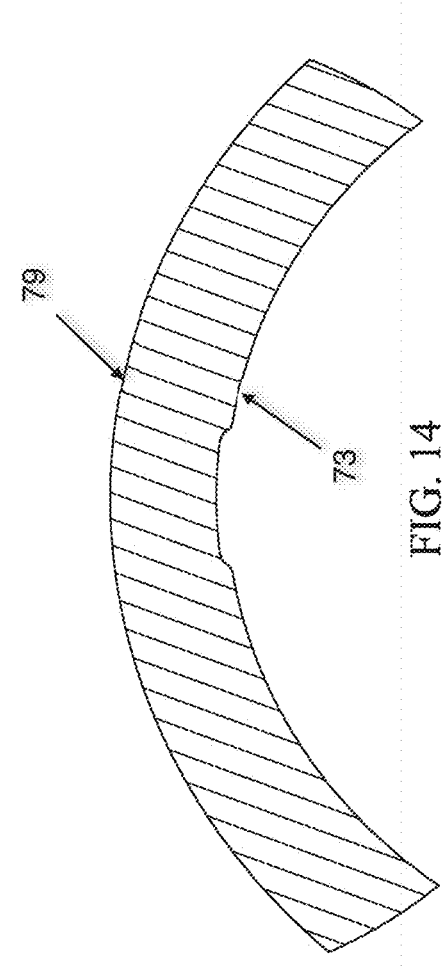

FIG. 14 is an enlarged view of the encircled area indicated in FIG. 11.

Figure 15:
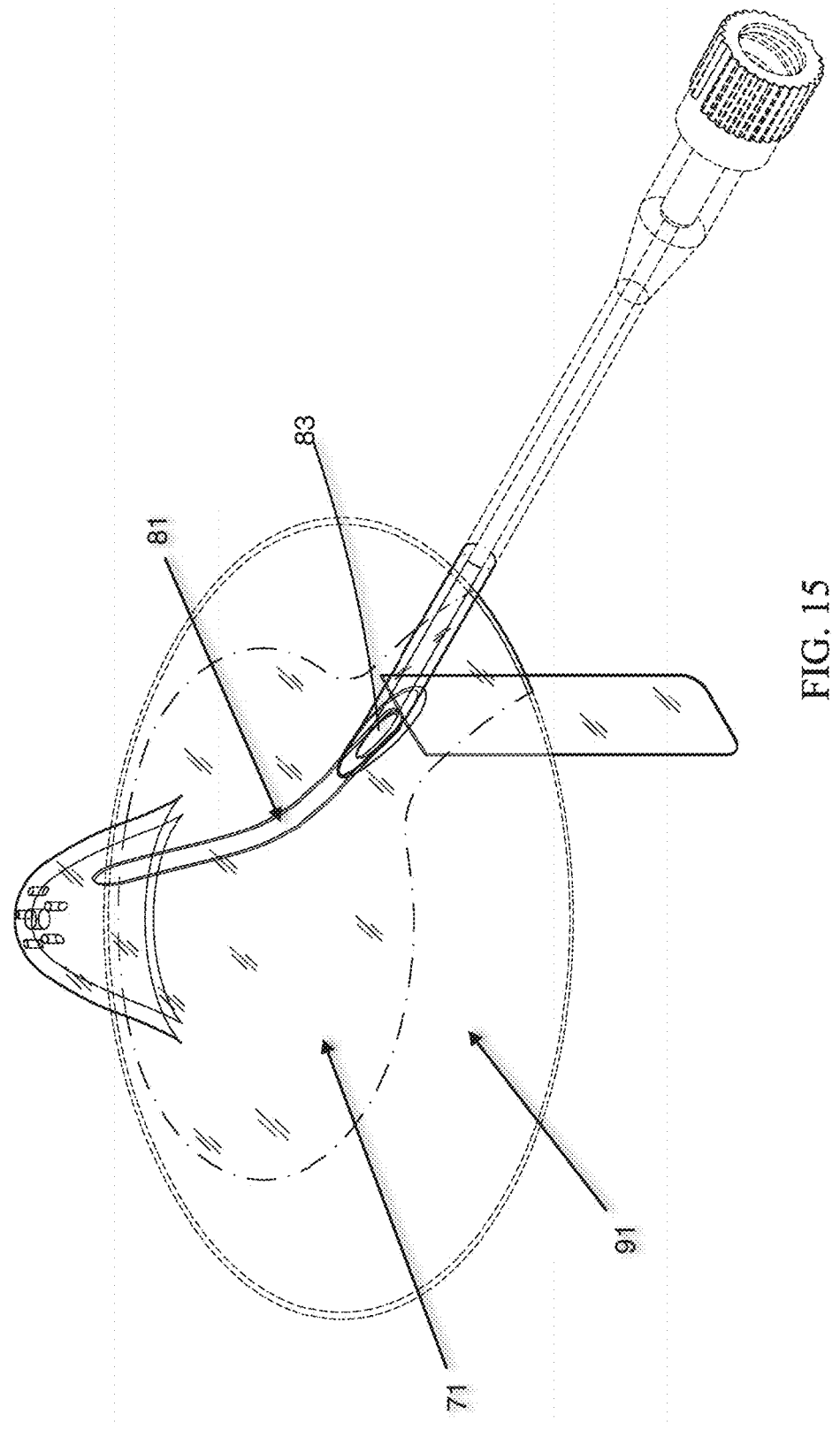
FIGS. 15-28 illustrate a partially assembled nipple shield with a loose flap that has not yet been bonded in place according to a second embodiment. The first and second embodiments are at least partially transparent as indicated in the figures.

FIG. 15 is a perspective view.

Figure 16:
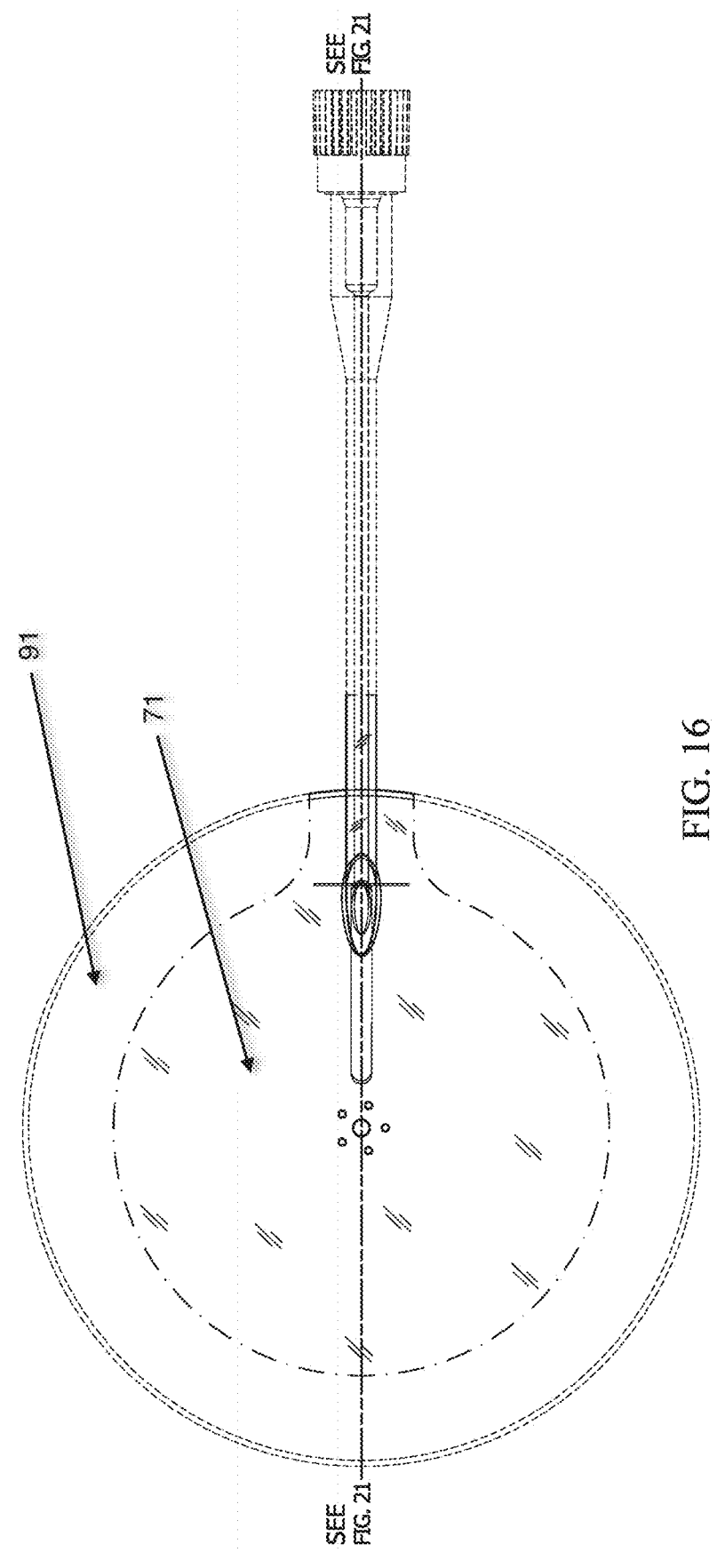

FIG. 16 is a top view (exterior).

Figure 17:
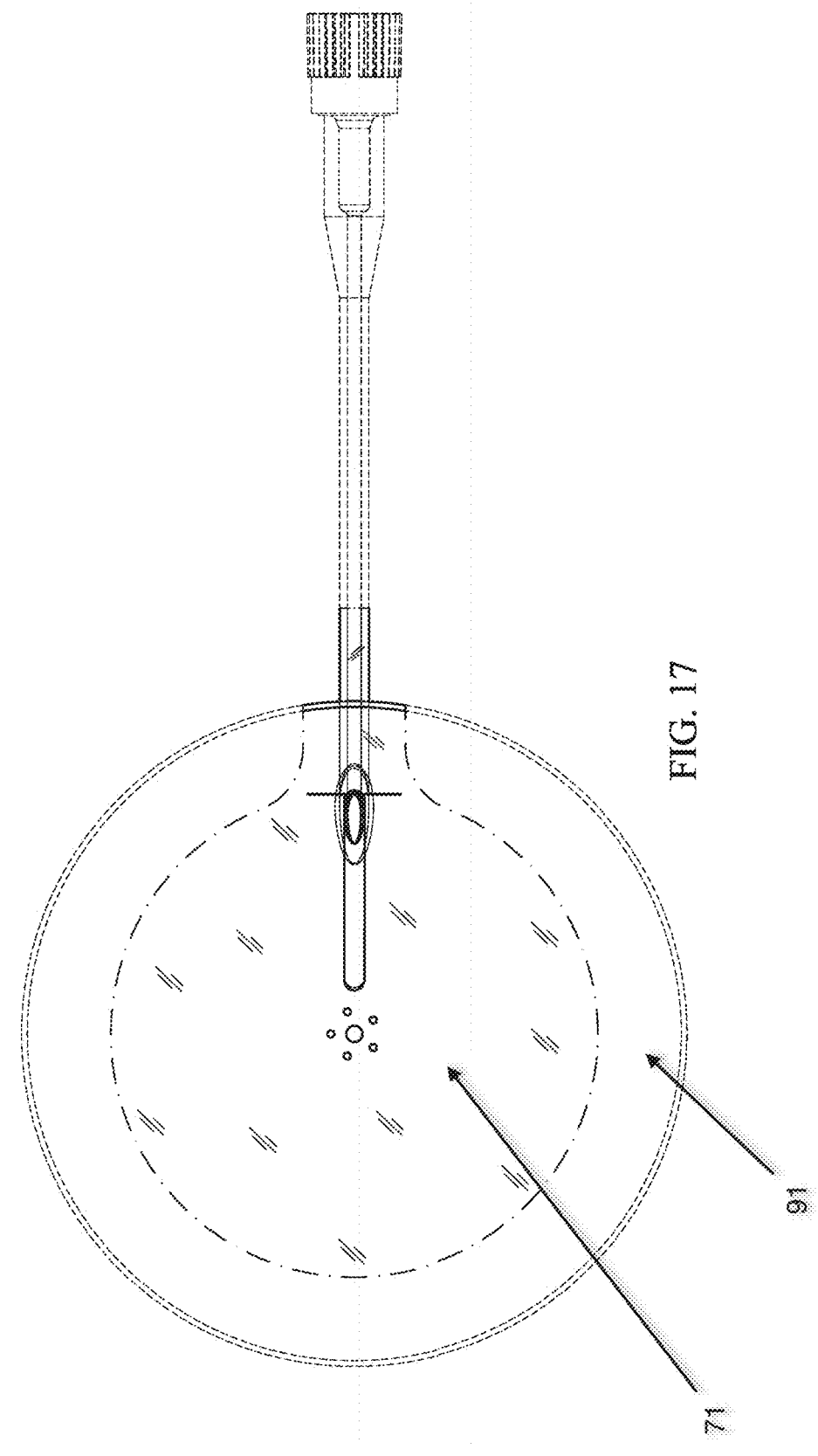

FIG. 17 is a bottom view (interior).

Figure 18:
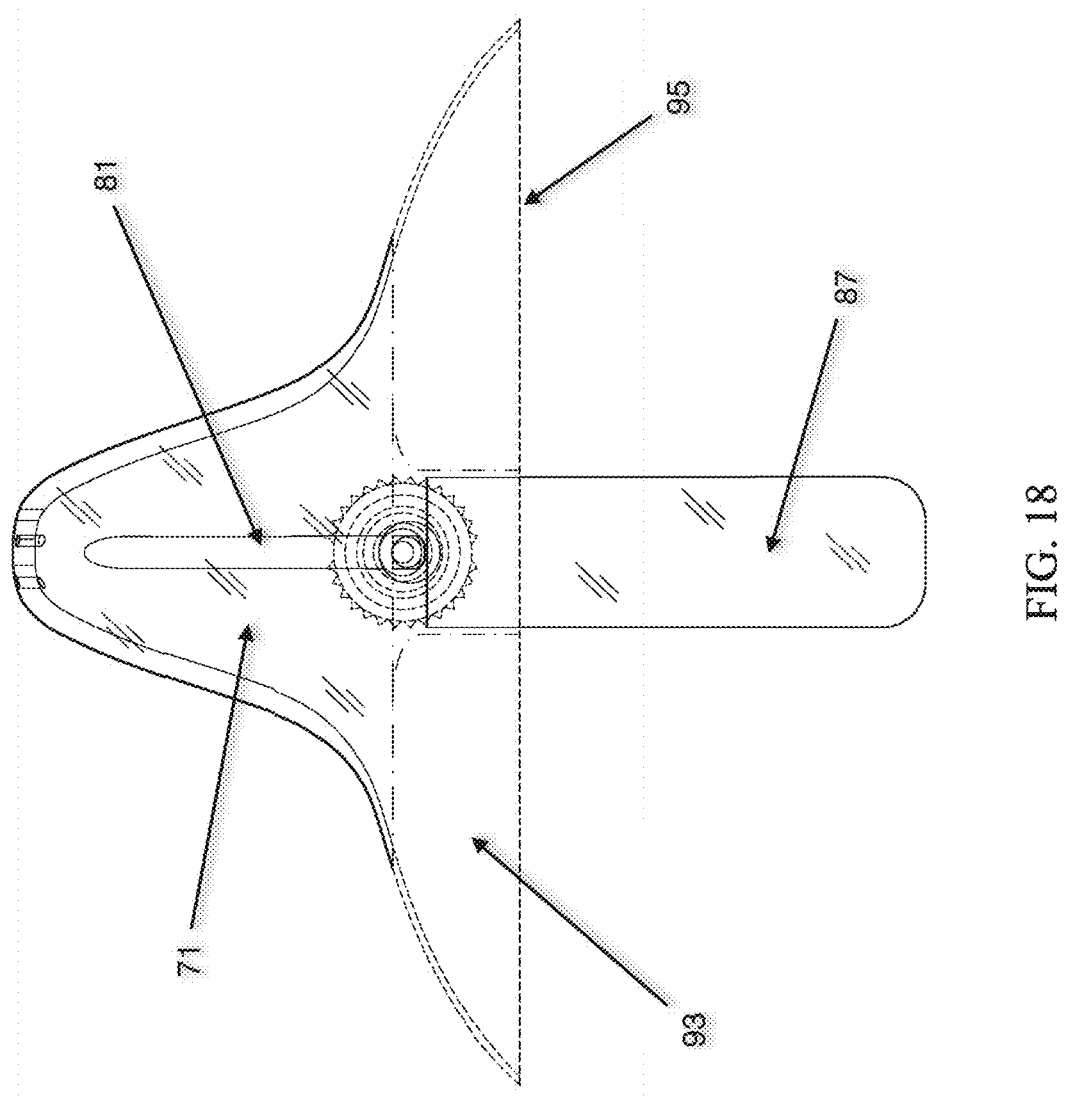

FIG. 18 is front view (opposite the port and tube).

Figure 19:
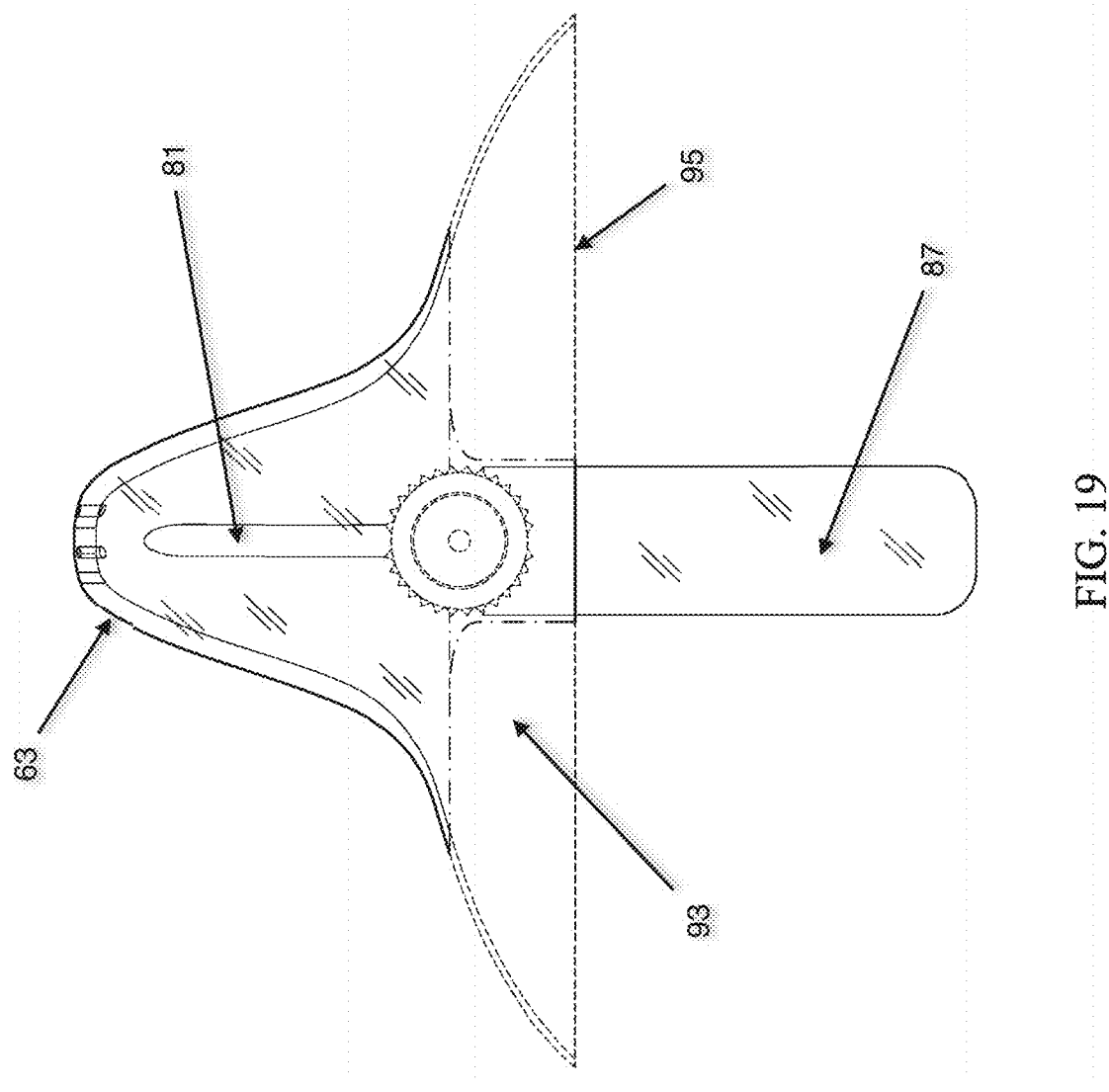

FIG. 19 is a back view (proximate the port and tube).

Figure 20:
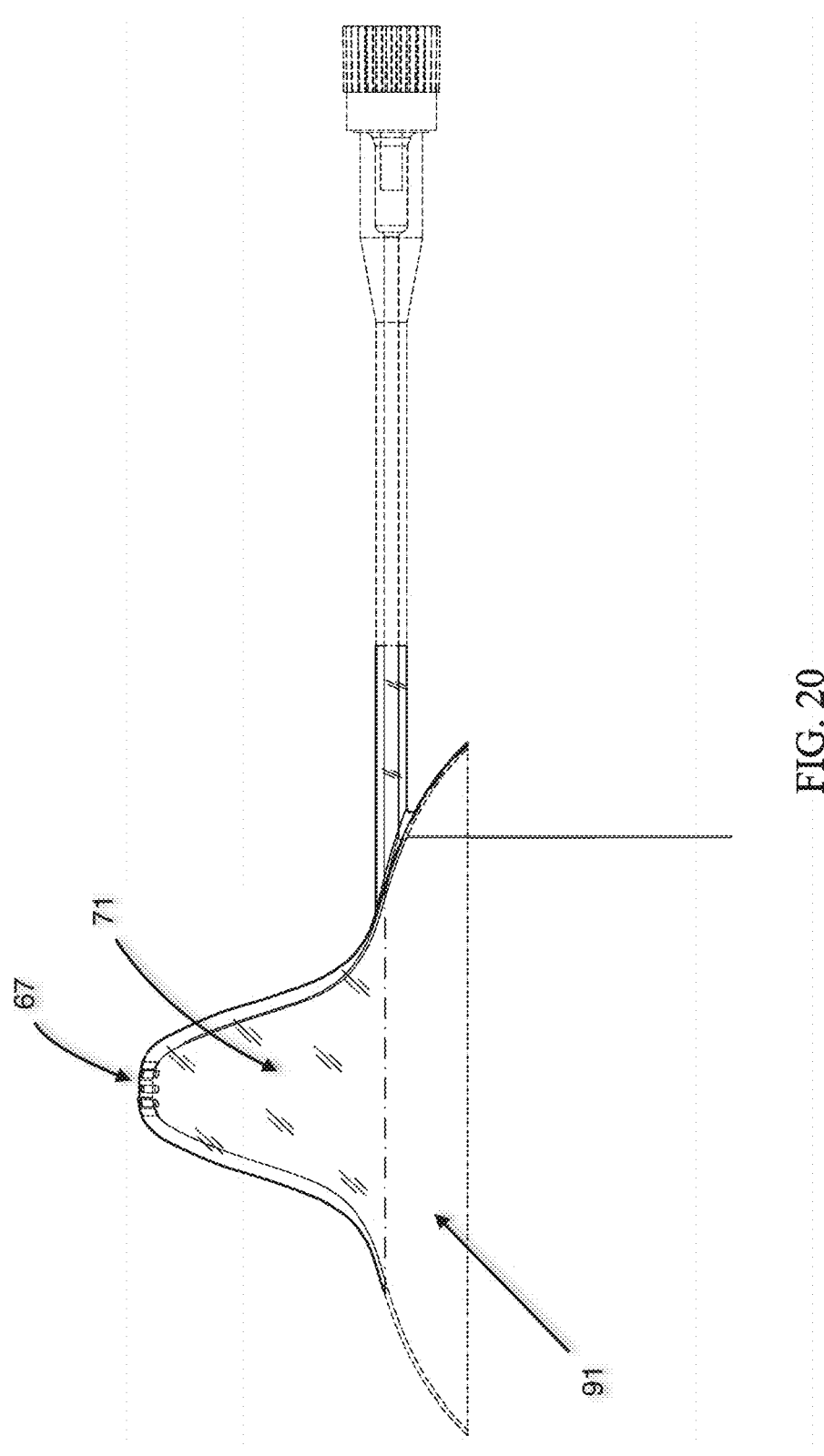

FIG. 20 is a right side view, and the left side view (not illustrated) is a mirror image of the right side view.

Figure 21:
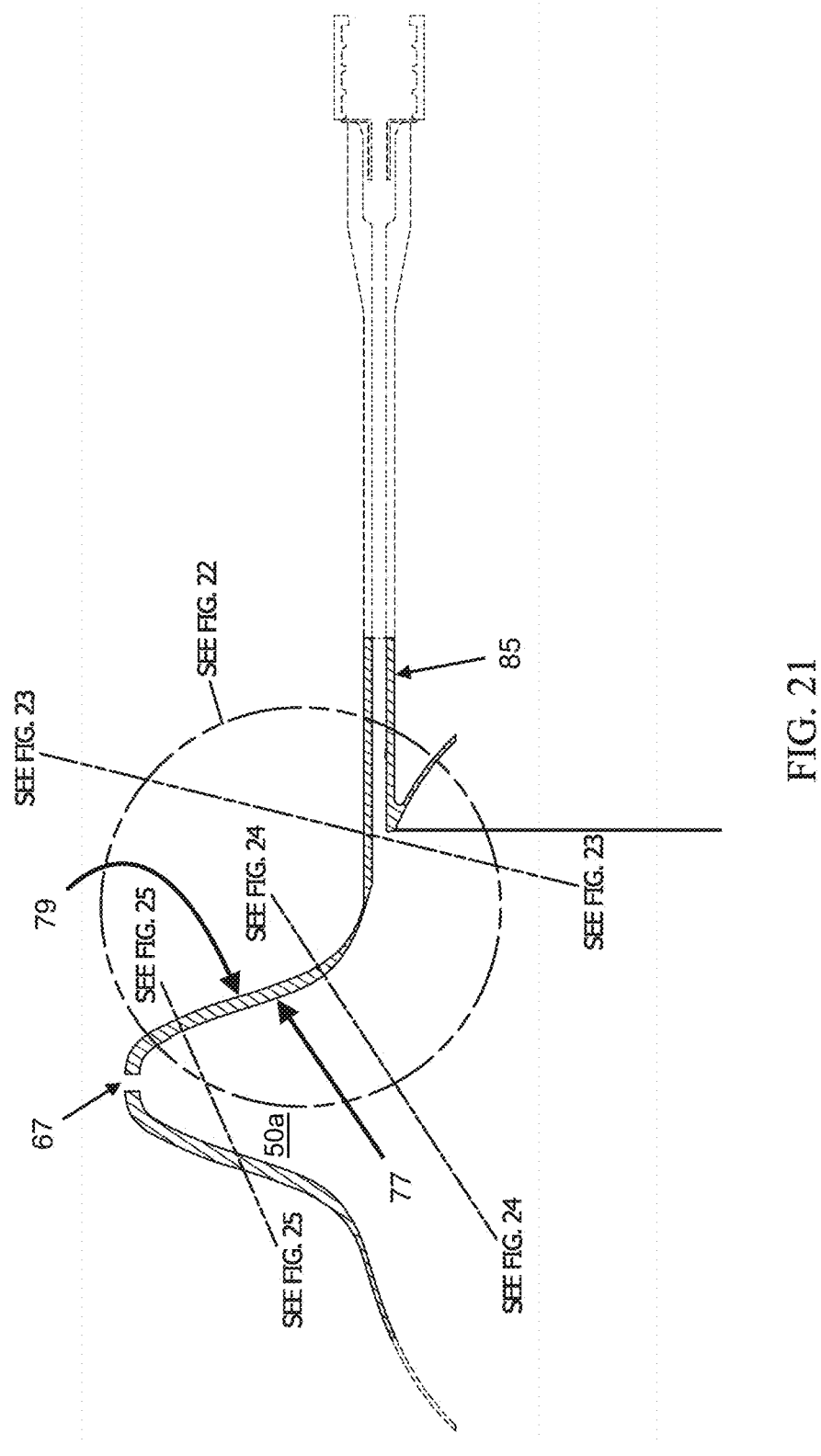

FIG. 21 is a cross-section view along the short-short-long dash line indicated in FIG. 16.

Figure 22:
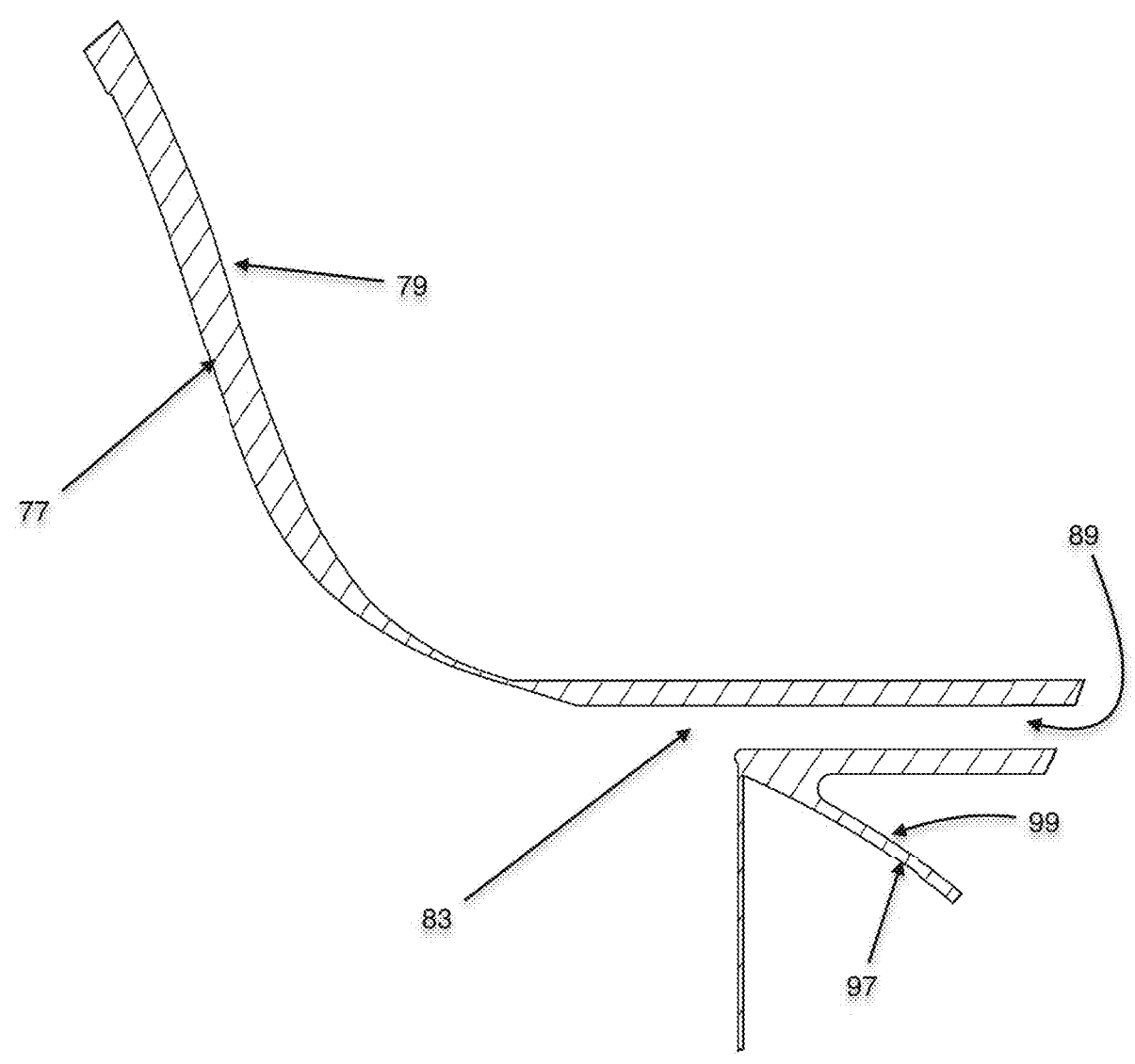

FIG. 22 is an enlarged view of the encircled area indicated in FIG. 21.

Figures 23, 24:
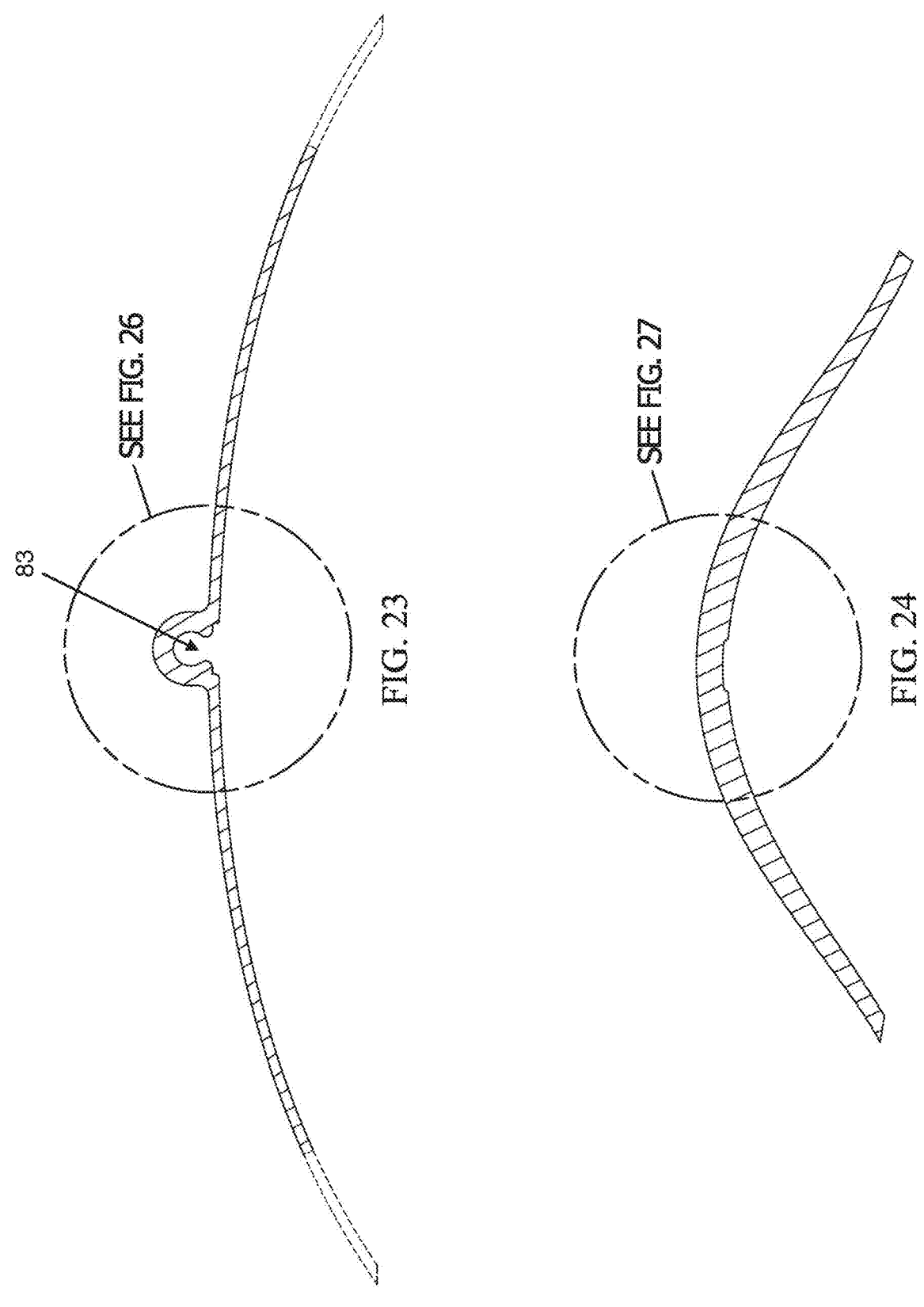

FIG. 23 is a cross-section view along the correspondingly numbered short-short-long dash line indicated in FIG. 21.

FIG. 24 is a cross-section view along the correspondingly numbered short-short-long dash line indicated in FIG. 21.

Figures 25, 26:
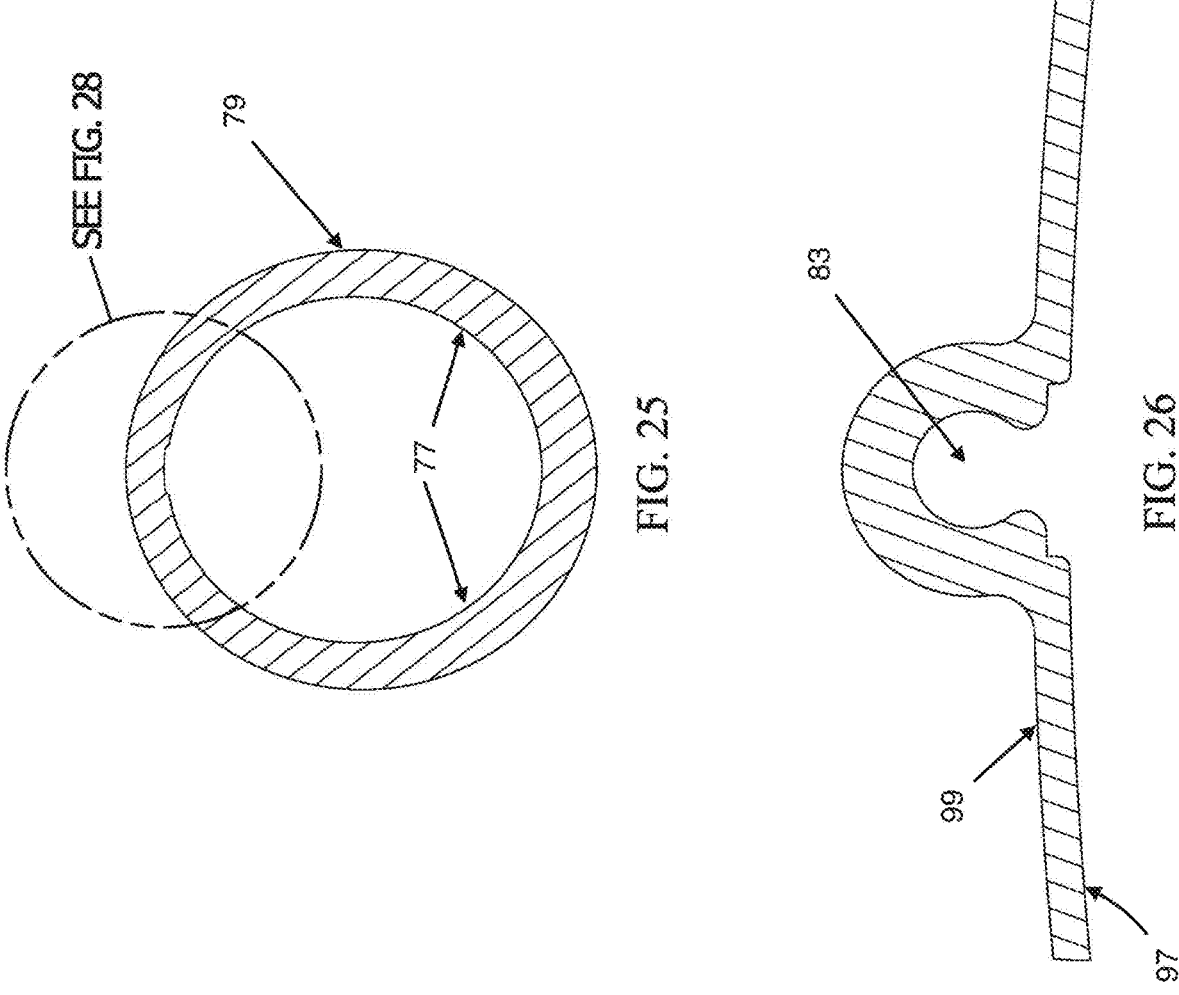

FIG. 25 is a cross-section view along the correspondingly numbered short-short-long dash line indicated in FIG. 21.

FIG. 26 is an enlarged view of the encircled area indicated in FIG. 23.

Figures 27, 28:
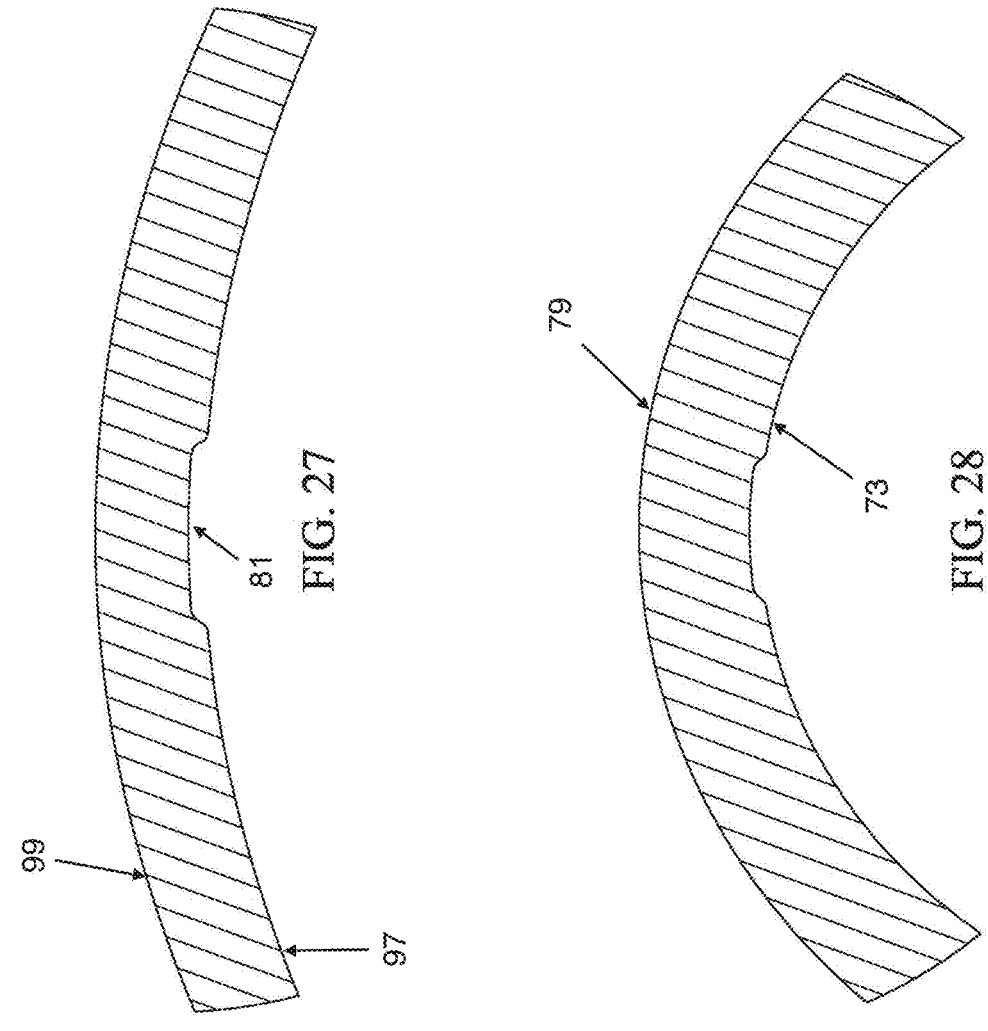

FIG. 27 is an enlarged view of the encircled area indicated in FIG. 24.

FIG. 28 is an enlarged view of the encircled area indicated in FIG. 25.

Figure 29:
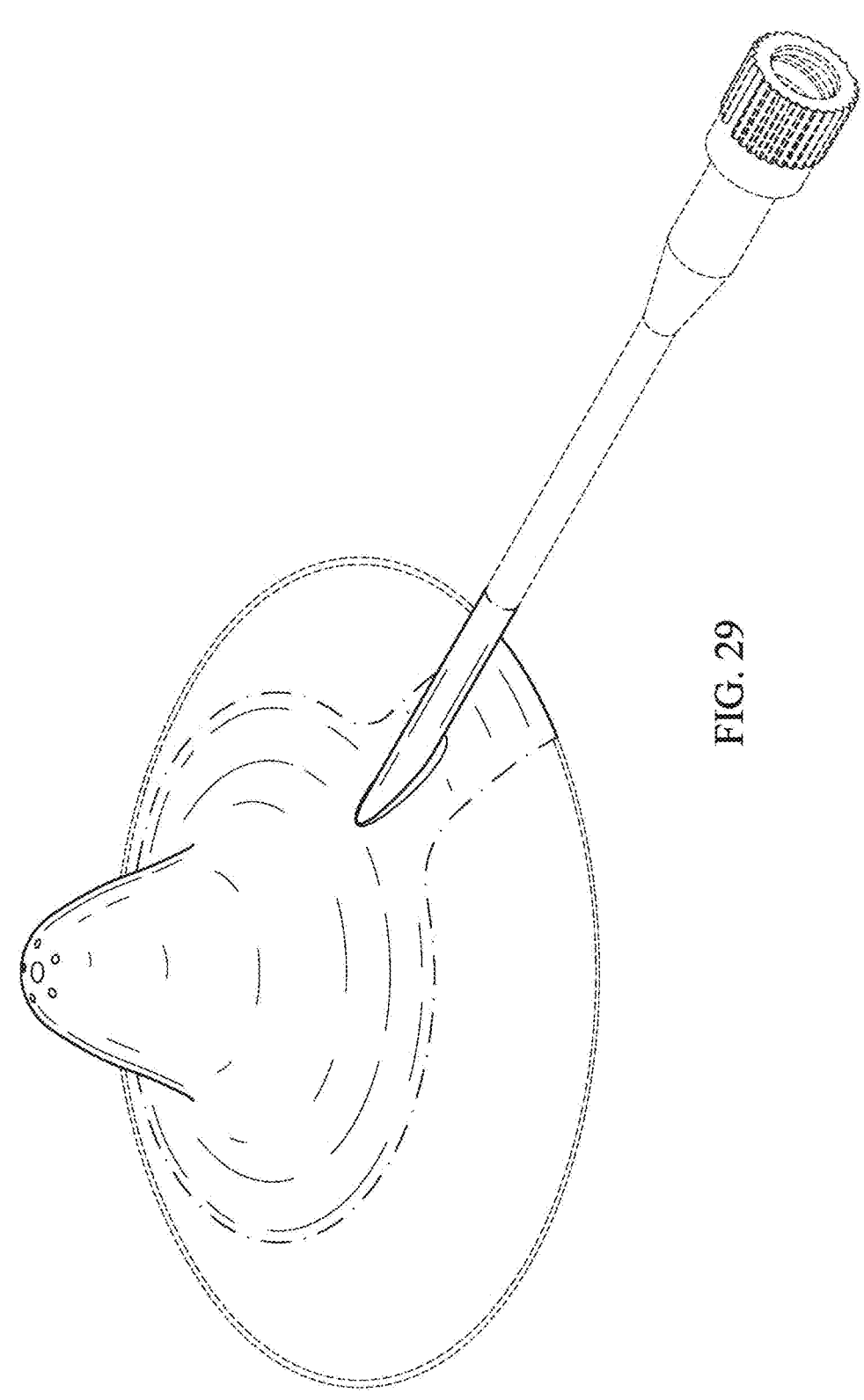
FIGS. 29-34 illustrate an assembled nipple shield that is generally opaque as indicated in the figures according to a third embodiment.

FIG. 29 is a perspective view.

Figure 30:
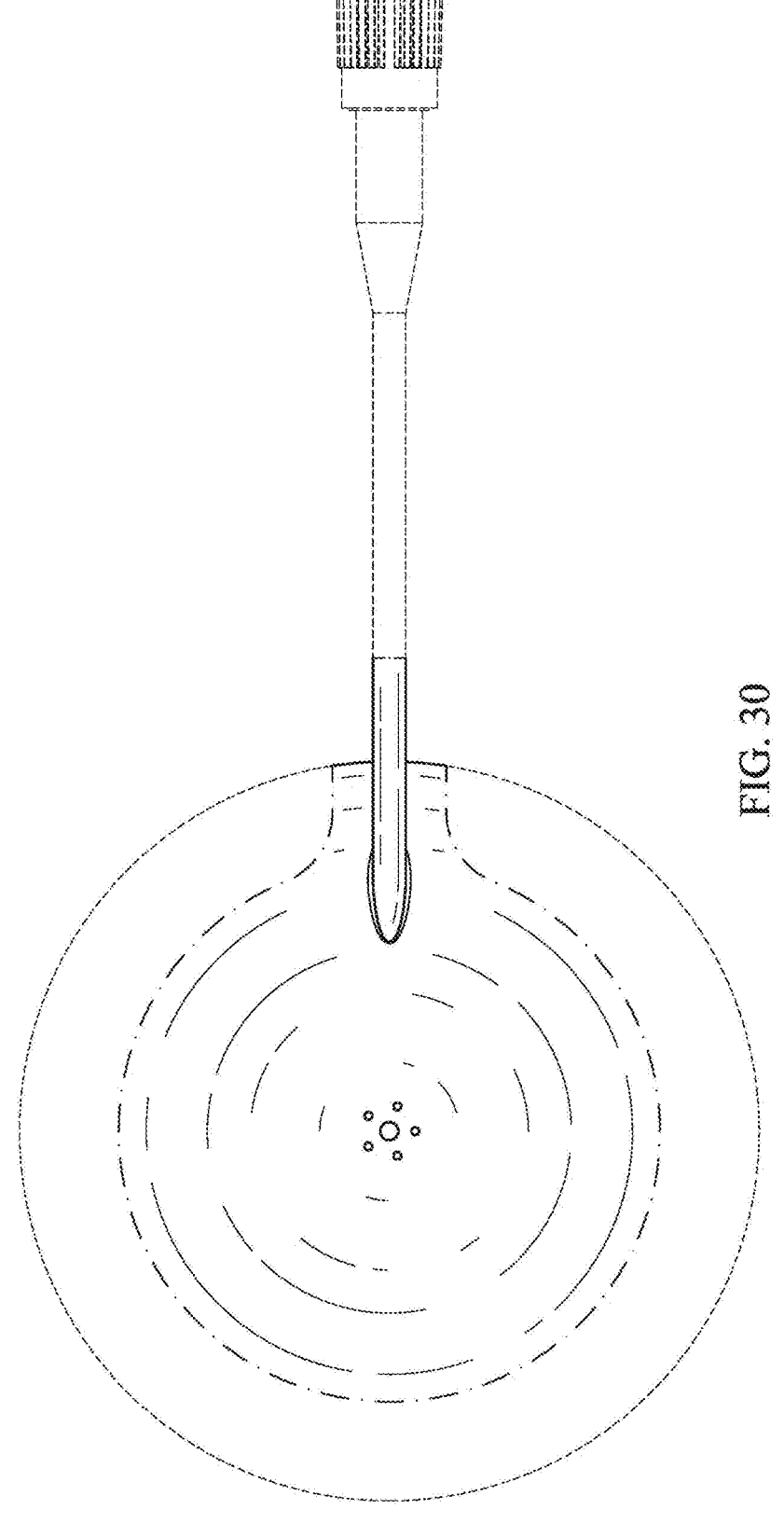

FIG. 30 is a top view (exterior).

Figure 31:
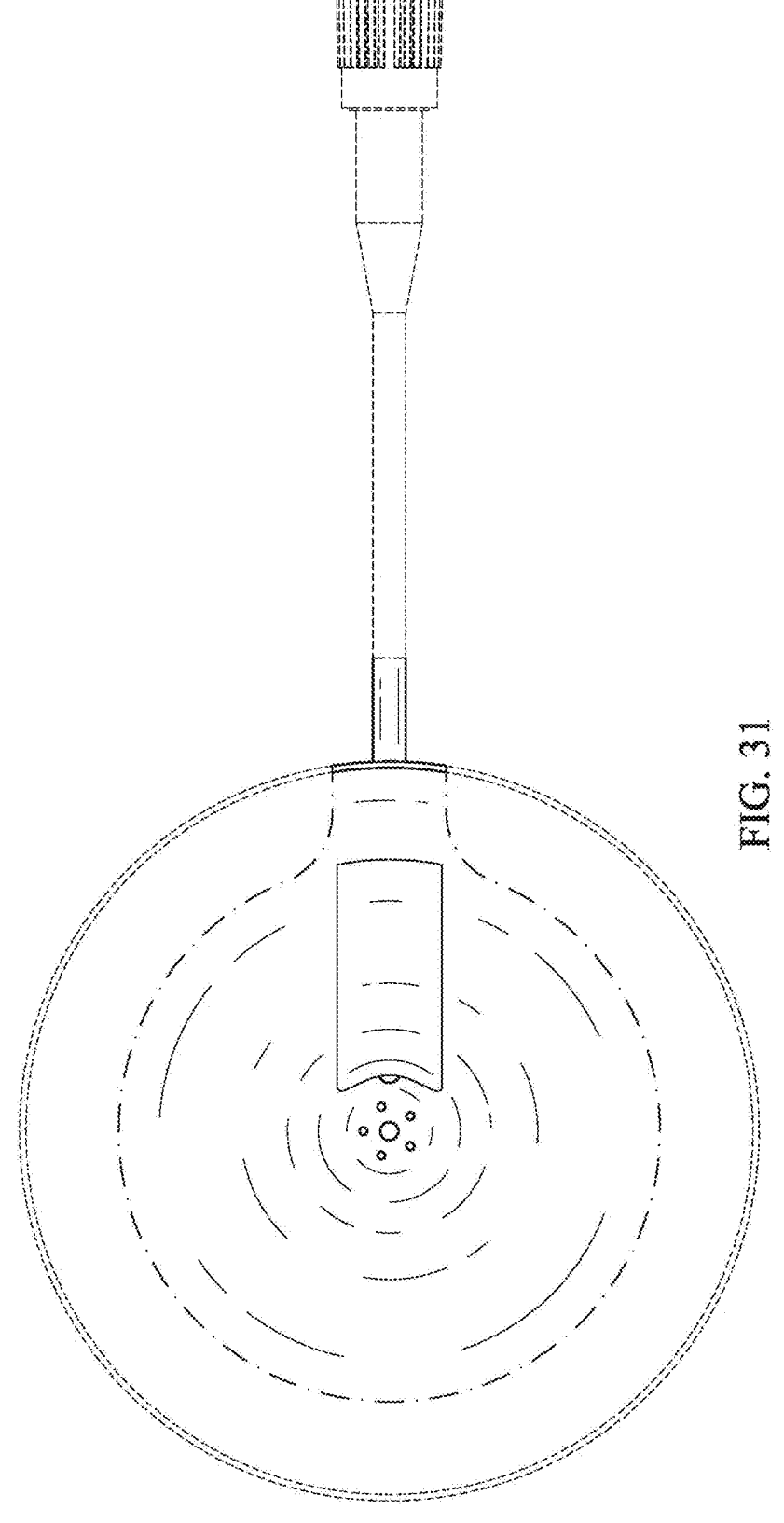

FIG. 31 is a bottom view (interior).

Figure 32:
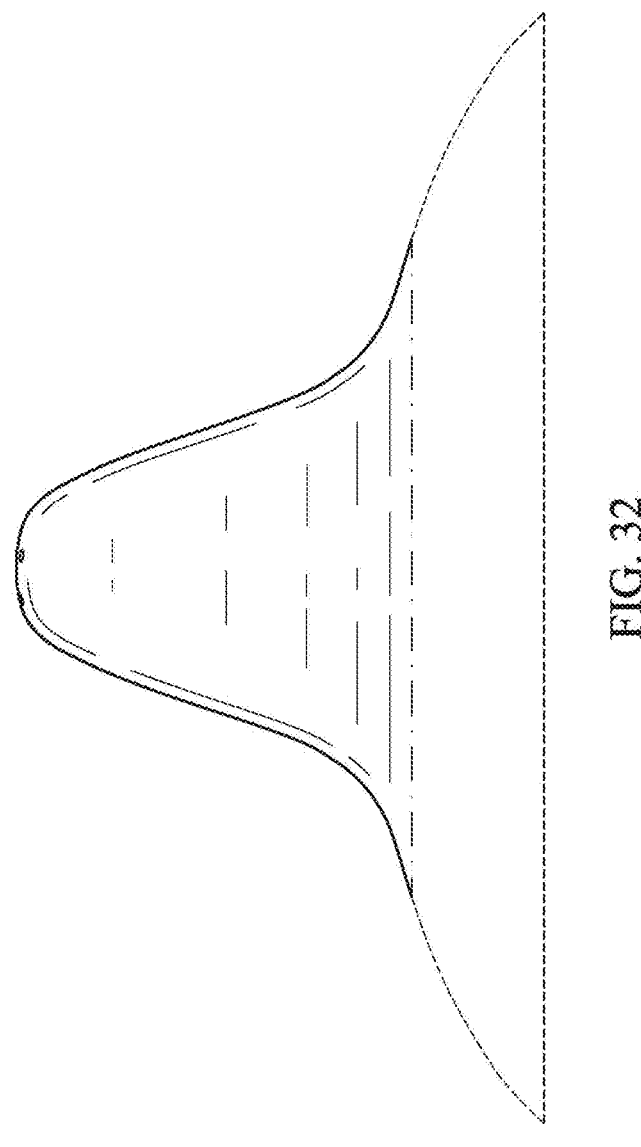

FIG. 32 is front view (opposite the port and tube).

Figure 33:
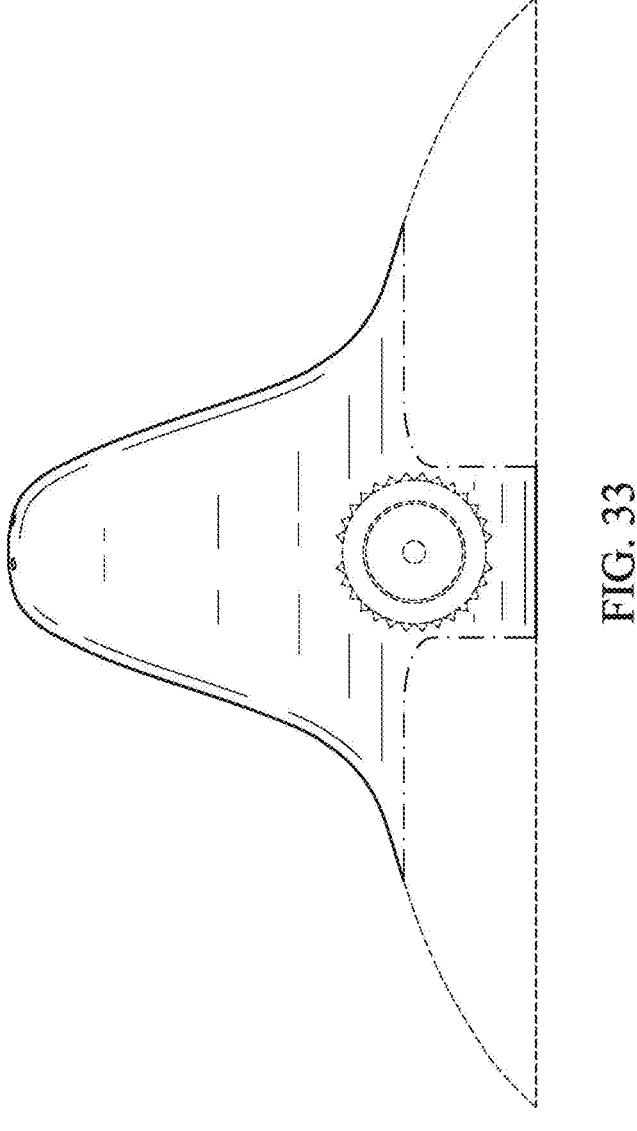

FIG. 33 is a back view (proximate the port and tube).

Figure 34:
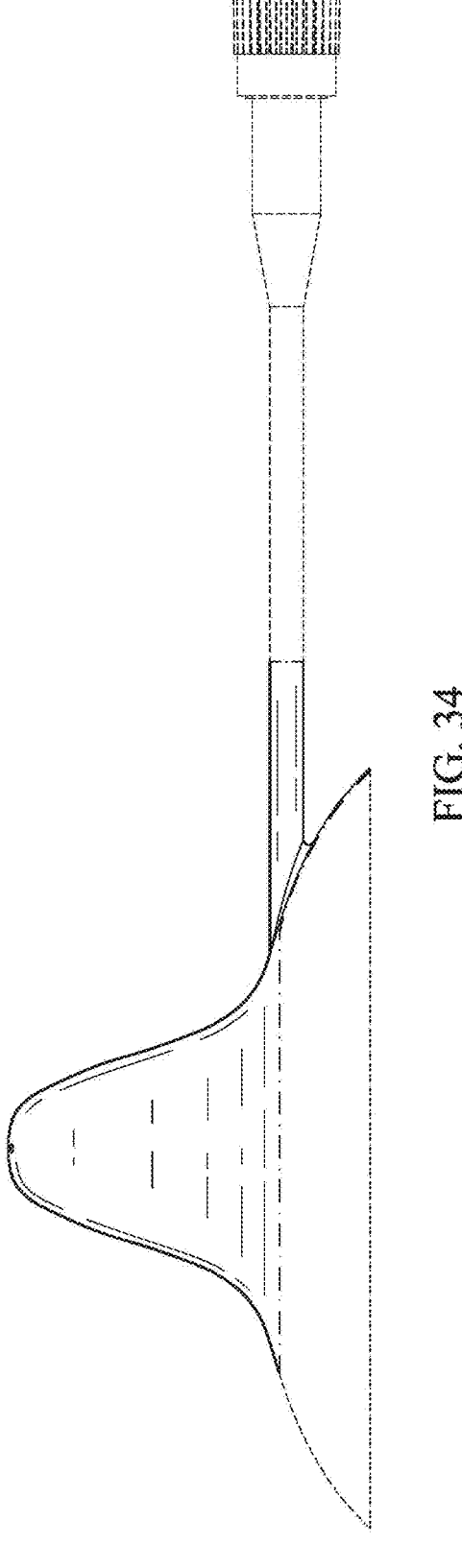

FIG. 34 is a right side view, and the left side view (not illustrated) is a mirror image of the right side view.

DETAILED DESCRIPTION

In the following description, references are made to various embodiments in accordance with which the disclosed subject matter can be practiced. Some embodiments may be described using the expressions one/an/another embodiment or the like, multiple instances of which do not necessarily refer to the same embodiment. Particular features, structures or characteristics associated with such instances can be combined in any suitable manner in various embodiments unless otherwise noted. By way of example, this disclosure may set out a set or list of a number of options or possibilities for an embodiment, and in such case, this disclosure specifically contemplates all clearly feasible combinations and/or permutations of items in the set or list.

An assembled embodiment of the present disclosure may generally be referred to as a nipple shield 50 as shown in FIGS. 1-6. Nipple shields 50 can be used by breastfeeding mothers to facilitate the feeding process. In accordance with various embodiments, the nipple shield 50 can include an open port 83 through which liquid supplement can flow from a supply tube 85 into an interior section of the nipple shield 50. The liquid supplement can be drawn through ports in a tip section 61 of the shield 50 in order to augment a naturally expressed flow of milk.

A flap of material which may be a channel cover 87 is shown in FIGS. 1 and 8 extending from the shield 50 in a second embodiment, and that is attached, in the various embodiments, to an interior portion of the nipple shield, such as an interior middle surface 77 or an interior lower surface 97 over an open channel 81 formed in the interior portion 50a of the shield 50 so as to form a closed or covered channel leading from an open port 83 to a location near an interior tip 63 of the shield 50. The flap of material 87 is also shown bonded in place in the third embodiment in FIG. 31.

In accordance with various embodiments, a nipple shield 50 can include the following features. The nipple shield 50 can include a tip section 61 having an interior tip surface 63, an exterior tip surface 65, and one or more perforations 67 passing through the tip section 61 between the interior tip surface 63 and the exterior tip surface 65. The nipple shield 50 can include a substantially frustoconical-shaped middle section 71 having a middle section upper portion 73 adjoining the tip section 61 and a middle section lower portion 75 opposite the upper portion 73. The middle section upper portion 73 preferably has a diameter less than that of the middle section lower portion 75, the middle section 71 having a substantially frustoconical-shaped interior middle surface 77 that adjoins the interior surface 63 of the tip section 61. The middle section 71 has a substantially frustoconical-shaped exterior middle surface 79 that adjoins the exterior surface 65 of the tip section 61, the middle section 71 having an open channel 81 formed as a groove or depression along the interior middle surface 77 and extending from the lower portion 75 to the upper portion 73 of the middle section 71. The nipple shield 50 may also include a lower section 91 having an upper portion 93 adjoining the middle section 71 and a lower section lower portion 95 opposite the lower section upper portion 93. The lower section 91 having an interior surface 97 that adjoins the interior surface 77 of the middle section 71, the lower section 91 having an exterior surface 99 that adjoins the exterior surface 79 of the middle section 71. The lower section 91 preferably has an open port 83 passing between the interior surface 97 and the exterior surface 99. The nipple shield 50 can include a supply tube 85 adjoining the lower section 91 at the open port 83 forming a passage through the supply tube 85 to the interior surface 97 of the lower section 91. The nipple shield 50 can include a channel cover 87 of thin flexible sheet material, the channel cover 87 being bonded, joined, affixed or sealed to portions of the interior surface 97 of the lower section 97 to cover the open port 83, the channel cover 87 being bonded, joined, affixed or sealed to portions of the interior surface 77 of the middle section 71 to cover a portion of the open channel 81, wherein the bonded, joined, affixed or sealed portions of the channel cover 87 extend along an interior surface 63, 77, 97 of the nipple shield 50 from the open port 83 and along two sides of the channel 87 to a location proximate the tip section 61.

In one embodiment, the interior surface 63 of the tip section 61 is concave and the exterior surface 65 of the tip section 61 is convex.

In one embodiment, the tip section 61, the middle section 71, and the lower section 91 are preferably formed of silicone rubber.

In one embodiment, the tip section 61, the middle section 71, the lower section 91, the supply tube 85, and the channel cover 87 are preferably formed of silicone rubber.

In one embodiment, the channel cover 87 is formed of a flap of material that is molded contiguously with at least the lower section 91, and wherein the molded flap channel cover 87 is subsequently bonded to the interior surface 77 of the middle section 71 along two sides of the open channel 81.

In one embodiment, the open channel 81 is omitted from the shield 50, such that the interior surface 77 of the middle section 71 does not include a channel 81, such that the channel cover 87 is not bonded to the interior surface 77 of the middle section 71 along a path where the open channel 81 would otherwise be located, and such that a stream of supplement flowing through the supply tube 85 and open port 83 can create a gap or passage and flow under pressure in an unbonded area between the channel cover 87 and the interior surface 77 of the middle section 71.

Although the subject matter has been described in terms of certain embodiments, other embodiments that may or may not provide various features and aspects set forth herein shall be understood to be contemplated by this disclosure. The specific embodiments described above are disclosed as examples only, and the scope of the patented subject matter is defined by the claims that follow. In the claims, a portion shall include greater than none and up to the whole of a thing.

The invention claimed is:

1. A nipple shield comprising:
   a tip section having an interior tip surface, an exterior tip surface and at least one perforation passing through the tip section between the interior tip surface and the exterior tip surface;
   a substantially frustoconical-shaped middle section having a middle section upper portion adjoining the tip section and a middle section lower portion opposite the middle section upper portion, the middle section upper portion having a diameter less than the middle section lower portion, the middle section having a substantially frustoconical-shaped interior middle surface that adjoins the interior tip surface, the middle section having a substantially frustoconical-shaped exterior middle surface that adjoins the exterior tip surface;
   a lower section having a lower section upper portion adjoining the middle section and a lower section lower portion opposite the lower section upper portion, the lower section having an interior lower surface that adjoins the interior middle surface, the lower section having an exterior lower surface that adjoins the exterior middle surface, the lower section having an open port passing between the interior lower surface and the exterior lower surface;
   a supply tube adjoining the lower section at the open port forming a passage through the supply tube to the interior lower surface; and
   a cover of flexible sheet material disposed on the interior lower surface and the interior middle surface so as to cover the open port, which cover extends from proximate to the open port in the lower section to proximate to the at least one perforation of the tip section, the cover being attached to portions of the interior lower surface proximate to the open port, wherein the cover is configured such that a stream of supplement from the supply tube can create a gap and flow under pressure from the open port to the tip section in an unattached area between the cover and the interior surface of the middle section.

2. The nipple shield of claim 1, wherein the interior tip surface is concave and the exterior tip surface is convex.

3. The nipple shield of claim 1, wherein the tip section, the middle section and the lower section are formed of silicone rubber.

4. The nipple shield of claim 1, wherein the tip section, the middle section, the lower section, the supply tube, and the cover are formed of silicone rubber.

5. The nipple shield of claim 1, wherein the cover is formed of a flap of material that is molded contiguously with at least the lower section, and wherein the molded flap is subsequently attached to the middle section along two side edges of the cover.

5

6

6. A nipple shield comprising:

a substantially frustoconical-shaped body having a lower section, a middle section, and a tip section, wherein the middle section has a diameter less than the lower section and the tip section has a diameter less than the middle section;

said frustoconical-shaped body being made of a rubber material and having an interior surface and an exterior surface spanning each of the lower section, the middle section, and the tip section;

at least one perforation in the tip section passing from the interior surface to the exterior surface;

an open port in the lower section passing from the exterior surface to the interior surface and a supply tube adjoining the exterior surface of the lower section so as to be in fluid communication with the open port; and a cover of flexible sheet material on the interior surface disposed over the open port and extending from proximate to the open port of the lower section to proximate to the tip section, wherein the cover is attached to the interior surface of the lower section and the interior surface of the middle section along two edges of the cover, and wherein the cover is configured such that a stream of supplement from the supply tube can create a gap and flow under pressure from the open port to the tip section in an unattached area between the cover and the interior surface of the middle section.

7. The nipple shield of claim 6, wherein the interior tip surface is concave and the exterior tip surface is convex.

8. The nipple shield of claim 6, wherein the tip section, the middle section and the lower section are formed of silicone rubber.

9. The nipple shield of claim 6, wherein the tip section, the middle section, the lower section, the supply tube, and the cover are formed of silicone rubber.

10. The nipple shield of claim 6, wherein the cover is formed of a flap of material that is molded contiguously with at least the lower section, and wherein the molded flap is subsequently attached to the middle section along two side edges of the cover.

* * * * *